United States Patent
Izatt et al.

(10) Patent No.: US 8,403,481 B2
(45) Date of Patent: Mar. 26, 2013

(54) METHODS, SYSTEMS AND COMPUTER PROGRAM PRODUCTS FOR DISTRIBUTED SCANNING FOR MOTION ARTIFACT REDUCTION IN OPTICAL COHERENCE TOMOGRAPHY

(75) Inventors: Joseph A. Izatt, Raleigh, NC (US);
Ryan P. McNabb, Durhham, NC (US);
Anthony N. Kuo, Durham, NC (US)

(73) Assignee: Duke University, Durham, NC (US)

( * ) Notice: Subject to any disclaimer, the term of this patent is extended or adjusted under 35 U.S.C. 154(b) by 95 days.

(21) Appl. No.: 13/010,517

(22) Filed: Jan. 20, 2011

(65) Prior Publication Data
US 2011/0222020 A1  Sep. 15, 2011

Related U.S. Application Data

(60) Provisional application No. 61/296,626, filed on Jan. 20, 2010.

(51) Int. Cl.
*A61B 3/14* (2006.01)
(52) U.S. Cl. .................. 351/206; 351/212; 351/246
(58) Field of Classification Search .......... 351/205, 351/206, 212, 246; 356/497
See application file for complete search history.

(56) References Cited

U.S. PATENT DOCUMENTS

| | | | |
|---|---|---|---|
| 7,336,366 B2 | 2/2008 | Choma et al. | |
| 7,633,627 B2 | 12/2009 | Choma et al. | |
| 7,695,140 B2 * | 4/2010 | Fercher | 351/221 |
| 7,697,145 B2 | 4/2010 | Izatt | |

OTHER PUBLICATIONS

Volker Westphal et al.; "Correction of geometric and refractive image distortions in optical coherence tomography applying Fermat's principle" (May 6, 2002) vol. 10, No. 9/Optics Express pp. 397-404.
Michael W. Belin, Md.; "Point/Counterpoint: The Pentacam Versus the Orbscan", Cataract & Refractive Surgery Today (Oct. 2006), pp. 80-84.

* cited by examiner

*Primary Examiner* — Jack Dinh
(74) *Attorney, Agent, or Firm* — Myers Bigel Sibley & Sajovec

(57) ABSTRACT

Methods of reducing motion artifacts in Optical Coherence Tomography (OCT) include scanning a sample with a scan pattern to acquire OCT data at a plurality of data locations. The data locations are distributed in the scan pattern across the sample such that at least some spatially adjacent data locations are acquired non-sequentially in time. A profile of the sample corresponding to a sample surface or an aspect of an internal structure of the sample is estimated responsive the OCT data.

30 Claims, 16 Drawing Sheets

Refractive Power of Corneal Surfaces:

$$P_a = \frac{n_1 - n_0}{R_a} \quad P_p = \frac{n_2 - n_1}{R_p} \quad P_t = P_a + P_p$$

Mean Keratometric Power (Approximation):

$$K = \frac{n_k - n_0}{R_a}$$

OBJ: 0.0000, 0.0000 DEG

IMA: 0.067, -0.001 MM

METHODS, SYSTEMS AND COMPUTER PROGRAM PRODUCTS FOR DISTRIBUTED SCANNING FOR MOTION ARTIFACT REDUCTION IN OPTICAL COHERENCE TOMOGRAPHY

RELATED APPLICATION

This application claims priority to U.S. Provisional Application Ser. No. 61/296626, filed Jan. 20, 2010, the disclosure of which is hereby incorporated by reference in its entirety.

STATEMENT OF GOVERNMENT SUPPORT

The present invention was produced in part using funds from the Federal Government under NIH grant no. R21 EY020001 entitled "Motion Artifact Reduced SDOCT of the Anterior Segment." The Federal government has certain rights in this invention.

FIELD OF THE INVENTION

The present invention relates to optical coherence tomography (OCT), and in particular, to methods and systems for motion artifact reduction in OCT.

BACKGROUND

Keratometry is measurement of the refractive power of the cornea. The refractive power of an optical surface or combination of optical surfaces is measured in Diopters (D), defined as the inverse of the focal length of the surface or combination measured in meters. Under the assumption that the corneal epithelial and endothelial surfaces are spherical, formulas for calculating the total corneal refractive power are as provided, e.g., in FIG. 2. Accurately calculating the total refractive power may utilize the radii of curvature of both the anterior and posterior surfaces. However, before tomographic techniques became available, the dominant technology for keratometry was corneal topography, which could only measure the anterior surface curvature. If it is assumed that the ratio of the anterior to posterior curvature is invariant, one can obtain a reasonably accurate approximation to the total corneal power (mean keratometric power) from the anterior surface alone by use of an empirically determined "keratometric refractive index," K. Calculation of corneal refractive power by measurement of the anterior segment radius of curvature over its central 3 mm and use of the keratometric index is the current clinical standard of care. This method has been reported to achieve ~0.25D accuracy, which is also the standard resolution of eyeglass prescriptions. Tang, M., Li, Y., Avila, M. and Huang, D. Measuring total corneal power before and after laser in situ keratomileusis with high-speed optical coherence tomography. J Cataract Refract Surg, 2006, 32(11), 1843-1850; Koch, D., Foulks, G., Moran, C. and Wakil, J. The Corneal EyeSys System: accuracy analysis and reproducibility of first-generation prototype. Refract Corneal Surg., 1989, 5, 424-429.

The keratometric index method of calculating corneal refractive index is invalid if the assumption of a constant ratio between anterior and posterior corneal curvatures is altered, as occurs after laser refractive surgery. In this case, direct measurement of both corneal surfaces may be necessary. An error in estimation of the axial sag of the corneal anterior surface (defined in FIG. 2 for the posterior surface) of approximately 40 μm at 1.5 mm radius from the optic axis may lead to 0.25D error; any tomographic technique should have at least this much accuracy to be competitive with topography.

Laser refractive surgery (LRS) is a popular elective procedure to help individuals reduce dependence on corrective eyewear. In the United States alone, over 7 million people have already received some form of LRS (LASIK, PRK, and other variants) making LRS one of the most commonly performed of all outpatient surgeries. It is estimated that an additional 700,000 people per year in the U.S. will continue to undergo the LASIK procedure to eliminate their need for glasses or contacts. American Society of Cataract and Refractive Surgery. ASCRS to Participate In and Co-Fund Study on Post-LASIK Quality of Life with U.S. Food and Drug Administration [press release]. 2008). LRS has typically been performed on adult individuals 20 to 40 years old. These millions of individuals have enjoyed close to 20/20 uncorrected visual acuity on average after LRS. Alio J L, M. O., Ortiz D, Perez-Santonja J J, Artola A, Ayala M J, Garcia M J, de Luna G C. Ten-Year Follow-Up of Laser In-Situ Keratomileusis for Myopia up to −10 Diopters. *Am J Ophthal*, 2008, 145, 46-54; Schallhorn S C, F. A., Huang D, Boxer Wachler B S, Trattler W B, Tanzer D J, Majmudar P A, Sugar A. Wavefront Guided LASIK for the Correction of Primary Myopia and Astigmatism: A Report by the American Academy of Ophthalmology. *Ophthalmology*, 2008, 115, 1249-1261. However, as all people age into late adulthood, vision invariably deteriorates from age related formation of cataracts, requiring cataract surgery for the restoration of functional vision. Based on a longitudinal study from 1995 to 2002, the estimated annual rate of cataract surgery for individuals older than 62 was 5.3%. Williams A, S. F., Lee P P. Longitudinal rates of cataract surgery. Arch Ophthalmol 2006, 124, 1308-1314. Thus, a projected 370,000 LRS patients will eventually require cataract surgery in at least one eye with a continuing need of about 37,000 per year after those initial patients.

Excimer laser refractive surgery ablates the anterior cornea to achieve a desired refractive correction for the patient. This alters the normal relationship between the anterior and posterior corneal curvatures critical to reflection based topography. Because accurate measurements of corneal power contribute to the proper selection of intraocular lenses needed after cataract surgery, patients who have had laser refractive surgery and subsequently underwent cataract surgery have had unanticipated and undesirable refractive outcomes. Seitz B, L. A., Nguyen N, Kus M, Kuchle M. Underestimation of Intraocular Lens Power for Cataract Surgery after Myopic Photorefractive Keratectomy. Ophthalmology, 1999, 106, 693-702. There continues to be no consensus method to overcome this limitation in accurately measuring corneal power after laser refractive surgery, and surgeons currently warn all these post-laser refractive surgery patients of potential "refractive surprises" after cataract surgery.

In cataract surgery, an artificial intraocular lens (IOL) is implanted to replace the refractive power lost from the removal of the natural lens (cataract). After modern cataract surgery, patients expect to be spectacle independent in part because of the accuracy in predicting the refractive power needed in the IOL. The predicted refractive power, however, depends critically on accurate measurements of the patient's total corneal refractive power ($P_t$; see FIG. 2). Physically, this parameter depends upon the curvature of the anterior (epithelial) and posterior (endothelial) surfaces of the cornea, as well as the indices of refraction of the intervening media (which are well known). Currently, the most widely used instruments to measure Pt are based on corneal topography, which estimate the refractive power of the cornea from measurements of the curvature of the front surface only. Assumptions are made regarding the refractive contribution of the posterior corneal surface. Klyce, S. Computer-assisted corneal topography. High-resolution graphic presentation and analysis of keratoscopy. Invest Ophthalmol Vis Sci, 1984, 25, 1426-1435. This approach provides satisfactory outcomes for patients with normal corneas, which have a predictable relationship between their front and back curvature. However, this assumption has proven flawed for the first patients who had LRS, subsequently underwent cataract surgery, and had unsatisfactory outcomes. Seitz B, L. A., Nguyen N, Kus M, Kuchle M. Underestimation of Intraocular Lens Power for Cataract Surgery after Myopic Photorefractive Keratectomy. Ophthalmology, 1999, 106, 693-702.

Since its introduction in the early 1990's, optical coherence tomography (OCT) has emerged as a promising imaging modality for micrometer-scale noninvasive imaging in biological and biomedical applications. Its relatively low cost and real-time, in vivo capabilities have fueled the investigation of this technique for applications in retinal and anterior segment imaging in ophthalmology (e.g., to detect retinal pathologies), early cancer detection and staging in the skin, gastrointestinal, and genitourinary tracts, as well as for ultrahigh resolution imaging of entire animals in embryology and developmental biology.

Conventional OCT systems are essentially range-gated low-coherence interferometers that have been configured for characterization of the scattering properties of biological and other samples. By measuring singly backscattered light as a function of depth, OCT fills a valuable niche in imaging of tissue ultrastructure, and provides subsurface imaging with high spatial resolution (~1-10 µm) in three dimensions and high sensitivity (>110 dB) in vivo with no contact needed between the probe and the tissue. OCT is based on the one-dimensional technique of optical coherence domain reflectometry (OCDR), also called optical low-coherence reflectometry (OLCR). See Youngquist, R. C., S. Carr, and D. E. N. Davies, *Optical Coherence Domain Reflectometry: A New Optical Evaluation Technique*. Opt. Lett., 1987. 12: p. 158; Takada, K., et al., *New measurement system for fault location in optical waveguide devices based on an interferometric technique*. Applied Optics, 1987. 26(9): p. 1603-1606; and Danielson, B. L. and C. D. Whittenberg, *Guided-wave Reflectometry with Micrometer Resolution*. Applied Optics, 1987. 26(14): p. 2836-2842. In some instances of time-domain OCT, depth in the sample is gated by low coherence interferometry. The sample is placed in the sample arm of a Michelson interferometer, and a scanning optical delay line is located in the reference arm.

The time-domain approach used in conventional OCT has been used in supporting biological and medical applications. An alternate approach involves acquiring as a function of optical wavenumber the interferometric signal generated by mixing sample light with reference light at a fixed group delay. Two methods have been developed which employ this Fourier domain (FD) approach. The first is generally referred to as Spectral-domain OCT (SDOCT). SDOCT uses a broadband light source and achieves spectral discrimination with a dispersive spectrometer in the detector arm. The second is generally referred to as swept-source OCT (SSOCT). SSOCT time-encodes wavenumber by rapidly tuning a narrowband source through a broad optical bandwidth. Both of these techniques can provide improvements in SNR of up to 15-20 dB when compared to time-domain OCT, because SDOCT and SSOCT capture the complex reflectivity profile (the magnitude of which is generally referred to as the "A-scan" data or depth-resolved sample reflectivity profile) in parallel. This is in contrast to time-domain OCT, where destructive interference is employed to isolate the interferometric signal from only one depth at a time as the reference delay is scanned.

Tomographic corneal imaging methods offer the ability to overcome the assumptions regarding the posterior curvature by directly measuring the posterior curvature. Three commercial clinical modalities are currently available: a slit-scanner based method (Bausch & Lomb Orbscan®), a time-domain based OCT (Carl Zeiss Meditec Visante®), and a rotating Scheimpflug photography based method (Oculus Pentacam®). The slit-scanner calculates the posterior surface mathematically from the front surface (Cairns G, M. C. Orbscan computerized topography: attributes, applications, and limitations. J Cataract Refract Surg, 2005, 31, 205-220), but there are questions regarding its ability to accurately represent the posterior surface. Donnenfeld, E. Discussion of article by Seitz B, Torres F, Langenbucher A, et al. *Ophthalmology*, 2001, 108, 673. The time-domain OCT instrument does not currently derive curvature information from its images. Because of these limitations and others, neither the slit-scanner nor time-domain OCT is generally used in clinical practice for quantitative evaluation of corneal curvature. The rotating Scheimpflug device takes 25 or 50 full diameter, radial pictures of the cornea and then reconstructs the anterior and posterior corneal surfaces from those photos. This device is used clinically for examining corneal curvature and deriving corneal power, though there is debate regarding the sufficiency of photographic resolution to accurately determine these parameters. None of these approaches appear capable of meeting the rapidly oncoming demand of millions of LRS patients who chose an elective procedure to obtain 20/20 vision and will now expect the same after modern cataract surgery.

Current clinical and research SDOCT systems generally feature about 5 µm axial resolution. Although this resolution is theoretically sufficient to calculate corneal refractive power with approximately 0.25D accuracy independent of the assumptions upon which corneal topography depend. However, conventional OCT imaging faces the additional technical hurdle that cross-sectional images are built up sequentially rather than simultaneously such that each sectional image is built up as the focused beam is scanned across the corneal surface. Despite utilization of a forehead rest in clinical SDOCT systems, it is difficult to immobilize the patient's head to better than about 10-100 µm during the 0.05 seconds required for acquisition of each standard SDOCT B-scan. Thus, as a sequential image is acquired, patient motion may corrupt the true profile of the corneal surfaces sufficiently to degrade the corneal power calculation beyond an acceptable level. Indeed, one OCT study published which quantified keratometric accuracy reported about 0.75D accuracy using moderate-speed OCT (2 kHz A-scan rate) alone. Tang, M., Li, Y., Avila, M. and Huang, D. Measuring total corneal power before and after laser in situ keratomileusis with high-speed optical coherence tomography. J Cataract Refract Surg, 2006, 32(11), 1843-1850.

SUMMARY

Methods of reducing motion artifacts in Optical Coherence Tomography (OCT) include scanning a sample with a scan pattern to acquire OCT data at a plurality of data locations. The data locations are distributed in the scan pattern across the sample such that at least some spatially adjacent data locations are acquired non-sequentially in time. A profile of the sample corresponding to a sample surface or an aspect of an internal structure of the sample is estimated responsive the OCT data.

In some embodiments, scanning the sample includes scanning the sample with a series of scanning lines such that at least one of the series of scanning lines is between two previously acquired scanning lines. The series of scanning lines may include a raster scan such that each of the series of scanning lines include a series of generally parallel scan lines, and at least one of the series of generally parallel scanning lines is between two previously acquired scanning lines. The series of scanning lines may include a series of radial scanning lines, and beginning locations of the series of radial scanning lines may define a generally circular shape. The at least one of the series of scanning lines that is between two previously acquired scanning positions may include at least one radial scanning line having a beginning location that is between a beginning location of two previously acquired scanning lines along the generally circular shape of beginning locations of the series of radial scanning lines.

In some embodiments, estimating a profile includes estimating a location of a peak of a normalized cross-correlation between spatially adjacent scans.

In some embodiments, estimating a profile includes ordering the OCT data in a spatial order.

In some embodiments, the OCT data is acquired in an ocular region having a diameter of about 6 mm during an acquisition time, and the data locations are temporally distributed so that a selected region having an area of about 0.2 mm$^2$ includes a subset of the plurality of data locations that is generally evenly distributed over the acquisition time.

In some embodiments, the OCT data is acquired in an area of the sample during an acquisition time, and the data locations are temporally distributed so that a selected region of the sample having an area of about one-tenth the area of sample includes a subset of the plurality of data locations that is generally evenly distributed over the acquisition time.

In some embodiments, the OCT data is acquired in an ocular region having a diameter of about 6 mm during an acquisition time, and the data locations are temporally distributed so that a selected region having an area of about 0.2 mm$^2$ includes a subset of the plurality of data locations that includes a number of data locations acquired during a first quarter of the acquisition time that is generally equal to a number of data locations acquired during a last quarter of the acquisition time.

In some embodiments, the OCT data is acquired in an area of the sample during an acquisition time, and the data locations are temporally distributed so that a selected region of the sample having an area of about one-tenth the area of sample includes a subset of the plurality of data locations that includes a number of data locations acquired during a first quarter of the acquisition time that is generally equal to a number of data locations acquired during a last quarter of the acquisition time.

According to some embodiments, an Optical Coherence Tomography (OCT) system includes an OCT scanner configured to scan a sample with a scan pattern to acquire OCT data at a plurality of data locations. The data locations are distributed in the scan pattern across the sample such that at least some spatially adjacent data locations are acquired non-sequentially in time. A profile estimation module is configured to estimate a profile of the sample corresponding to a sample surface or an aspect of an internal structure of the sample responsive the OCT data.

In some embodiments, a computer program product for reducing motion artifacts in an Optical Coherence Tomography (OCT) system is provided. The computer program product includes a computer readable medium having computer readable program code embodied therein. The computer readable program code includes computer readable program code that is configured to scan a sample with an OCT scanner using a scan pattern to acquire OCT data at a plurality of data locations. The data locations are distributed in the scan pattern across the sample such that at least some spatially adjacent data locations are acquired non-sequentially in time. Computer readable program code is configured to estimate a profile of the sample responsive the OCT data.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3A illustrates M-scan data comprising 100,000 repeated A-scans acquired at the same location near the apex of a subject's cornea. The integration time per A-scan was 50 μs, thus the total acquisition time was 5 s. FIG. 3B illustrates axial corneal motion was estimated by normalized cross-correlation of the data in FIG. 3A with this kernel obtained by averaging the first 50 A-scans. FIG. 3C is a result of cross-correlation analysis comprising an estimate of axial patient motion over the 5 s acquisition period. Maximum (peak-peak) motion of ~70 μm was observed over the 5 s acquisition. FIG. 3D illustrates a scaled amplitude spectrum of the patient motion data. The peak motion with amplitude of ~30 μm occurred at a frequency of ~0.7 Hz, likely due to subject heartbeat. Ignoring sharp data acquisition artifacts at harmonics of the M-scan frame rate of 20 Hz, the patient motion drops well below 1 μm amplitude for frequencies above ~50-100 Hz.

FIGS. 5A-5J illustrate 10 A-scans per B-scan (or only 10 B-scans per volume acquisition; however, it should be understood that the techniques may be expanded for any number of A-scans and B-scans.

FIG. 6A is a reconstructed corneal scan showing patient motion over the entire acquisition interval. The image consists of sequential groups of 3 A-scans extracted from sequential B-scans. FIG. 6B is an alternate reconstructed corneal scan which encodes patient motion into high spatial frequencies. This scan was constructed from sequential groups of 3 A-scans from each B-scan, however the 3 selected A-scans were distributed across the entire dataset. FIG. 6C is B-scan obtained by low-pass spatial filtering of data from FIG. 6B illustrates reconstruction of accurate corneal profile with patient motion artifact removed. The choice of low-pass cutoff frequency comprises a trade-off between rejecting temporal frequency-induced artifacts and preserving actual spatial profile information.

FIG. 7A illustrates a prism for spectral dispersion correction. The prism is a double-Amici design with a center wavelength of 828 nm. FIG. 7B illustrates a design for clinical use such that in an effort to reduce space, a diffraction grating (DG) is used for spectral dispersion. CL—Collimating Lens; DG—Diffraction Grating; OR—Optical Relay; AOD—Acousto-Optic Deflector pair; FM—Folding Mirror; DRHL—Diffractive-Refractive Hybrid Lens; Cornea—Patient corneal epithelium.

DETAILED DESCRIPTION OF EMBODIMENTS OF THE INVENTION

Figure 1:
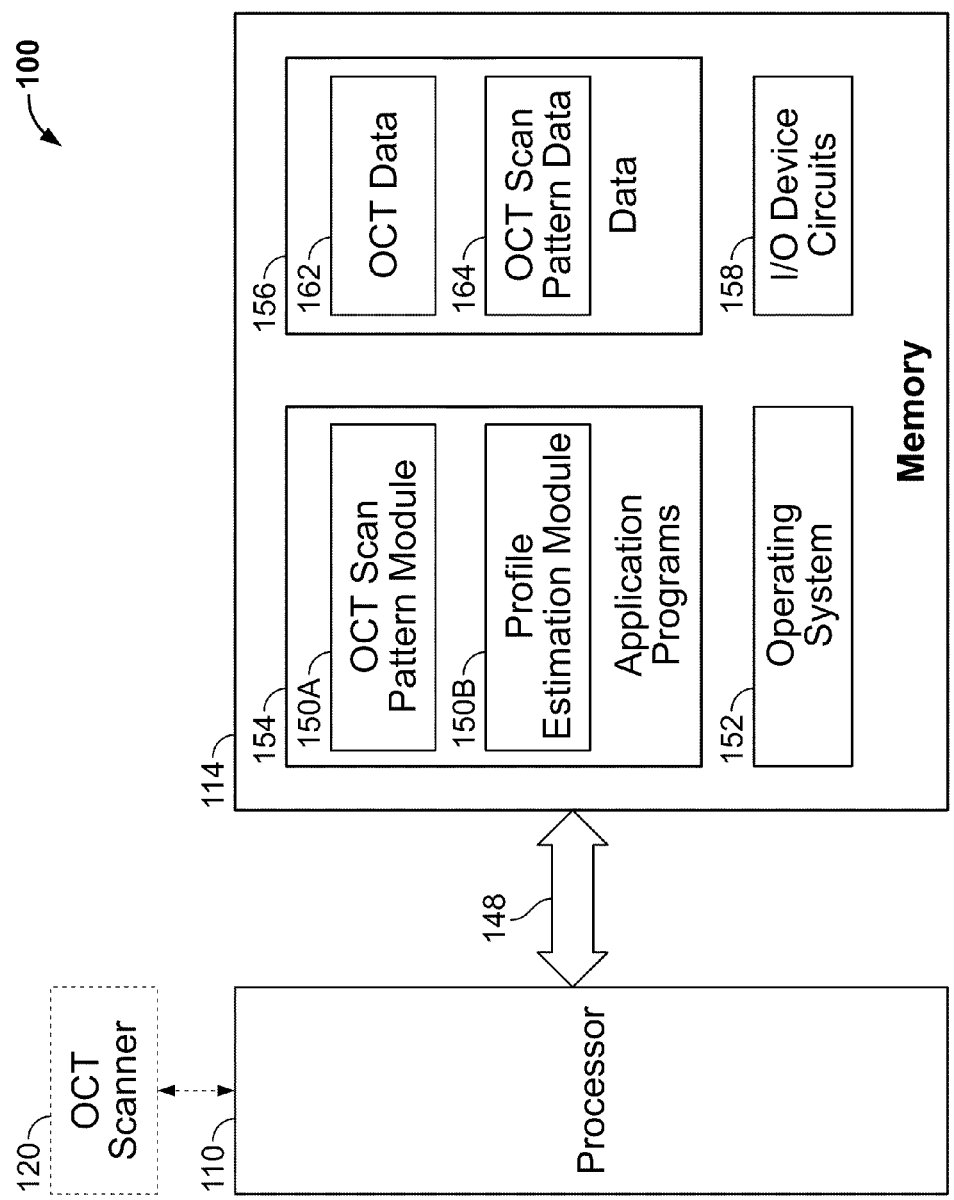
FIG. 1 is a block diagram illustrating an OCT scanning system according to some embodiments of the present invention.
Figure 2:
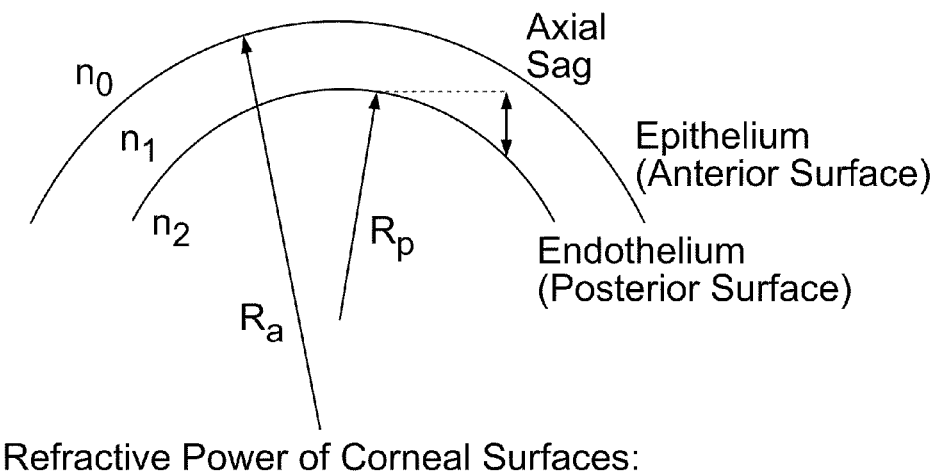
FIG. 2 is a block diagram illustrating a calculation of refractive powers for an anterior surface ($P_a$), a posterior surface ($P_p$), exact total corneal power ($P_t$) and the keratometric approximation to the total corneal refractive power (K). $R_a$ and $R_p$ are the radii of the (assumed spherical) corneal anterior and posterior surfaces, respectively. The relevant refractive indices are $n_0$=1.0 (air), $n_1$=1.376 (corneal stroma), $n_2$=1.336 (acqueous humor), and $n_k$=1.3375 (keratometrix index).

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, electromagnetic, or semiconductor system, apparatus, or device. More specific examples (a non-exhaustive list) of the computer-readable medium would include the following: a portable computer diskette, a random access memory (RAM), a read-only memory (ROM), an erasable programmable read-only memory (EPROM or Flash memory), an optical fiber, and a portable compact disc read-only memory (CD-ROM).

In some embodiments, motion artifacts in Optical Coherence Tomography (OCT) may be reduced by scanning a sample with a scan pattern to acquire OCT data at a plurality of data locations. The data locations are distributed in the scan pattern across the sample such that at least some spatially adjacent data locations are acquired non-sequentially in time. At least one spatial profile of the sample corresponding to one of its surfaces or an aspect of its internal structure may be estimated responsive to the OCT data. Accordingly, a scan pattern may be selected so that OCT data in a local region of the sample is distributed over a time range such that the structure of the sample is encoded into high spatial frequency content of the image data that may be separated from the motion artifact, e.g., via high-pass filtering.

FIG. 1 is a block diagram of exemplary embodiments of an OCT control system 100 according to embodiments of the present invention. As shown in FIG. 1, in some embodiments, the system 100 includes memory 114, a processor 110 and is communicatively coupled to an OCT scanner 120, which may be used to interact with the processor 110 and memory 114. The processor 110 communicates with the memory 114 via an address/data bus 148. As may be appreciated by one of skill in the art, the processor 110 may be any commercially available or custom microprocessor. Memory 114 is representative of the overall hierarchy of memory devices containing software and data used to implement the functionality of the crop management system 100. Memory 114 can include, but it not limited to, the following types of devices: cache, ROM, PROM, EPROM, EEPROM, flash memory, SRAM and DRAM.

As shown in FIG. 1, the memory 114 may comprise several categories of software and data: an operating system 152, applications 154, data 156 and input/output (I/O) device drivers/circuits 158.

As may be appreciated by one of skill in the art, the system 100 may use any suitable operating system 152, including, but not limited to, Windows NT, Windows2007 or Windows Vista from Microsoft Corp. (Redmond, Wash.), Mac OS from Apple, Inc. (Cupertino, Calif.), Unix or Linux.

The applications 154 may include one or more programs configured to implement one or more of the various features of the present invention. The applications 154 may include an OCT scan pattern module 150A and/or a profile estimation module 150B as described herein.

Data 156 may include static and/or dynamic data used by the operating system 152, applications 154, I/O device drivers 158 and other software components. Data 156 may include an OCT data 162 including information collected from the OCT scanner 120, and OCT scan pattern data 164 including scan patterns for scanning a sample with the OCT scanner 120. I/O device drivers 158 typically comprise software routines accessed through the operating system 152 by the applications 154 to communicate with devices such as I/O ports, memory 114 components and/or the remote devices 120.

Although embodiments of the present invention are illustrated, for example, with reference to the OCT scan module 150A and the profile estimation module 150B being an application program in FIG. 1, as may be appreciated by those of skill in the art, other configurations may also be utilized that are still within the scope of the present invention. For example, the OCT scan pattern module 150A and/or the profile estimation module 150B may also be incorporated into the operating system 152, the I/O device drivers 158 or other such logical division of the data processing system 100. Moreover, some or all of the operations of the OCT scan pattern module 150A and/or the profile estimation module 150B described herein may be incorporated into the OCT scanner 120. Thus, the present invention should not be construed as limited to the configuration of FIG. 1, which is intended to encompass any configuration capable of carrying out the operations described herein.

In some embodiments, the OCT scan pattern module 150A may control a scan pattern of the OCT scanner 120, e.g., by using scan patterns from the OCT scan pattern data 164. Typical conventional OCT scan patterns include raster scanning (a pattern having a generally rectangular grid of data locations or pixels) or radial scanning (a scan having scan lines that intersect at a common point and intersect radially). According to embodiments of the present invention, scan patterns may be used that distribute OCT data locations across the sample such that spatially adjacent data locations are acquired non-sequentially in time. For example, the sample may be scanned with a series of scanning lines such that some of the series of scanning lines are between two previously acquired scanning lines. The scanning lines may include a raster scan having a series of generally parallel scan lines. As another example, a series of radial scanning lines may be used so that the beginning locations of the series of radial scanning lines may define a generally circular shape. Instead of acquiring the radial scanning lines sequentially around the generally circular shape defined by the beginning locations of the scanning lines, radial scan lines may be acquired non-sequentially such that some of the scanning lines have a beginning location that is between beginning locations of two previously acquired scanning lines along the generally circular shape.

It should be understood that any scanning pattern may be used, including scanning patterns that are non-sequentially acquired, so that the data locations are temporally distributed so that selected regions within the sample include a subset of data that is generally evenly distributed over the acquisition time. In this configuration, the spatial profile of the sample may be determined, for example, with the profile estimation module 150B by reordering the data according to a spatial order and/or using a filter or other averaging method, so that time dependent motion artifacts are reduced or eliminated from the spatial profile.

For example, the data locations of the OCT data may be temporally distributed so that a selected local region of the sample having an area of about one-tenth the area of the scanned sample or more may include a subset of the data locations that is generally evenly distributed over the acquisition time of the sample area. For an ocular region, such as a cornea having a diameter of about 6 mm, the data locations may be temporally distributed so that any area of about 0.05 $mm^2$, 0.1 $mm^2$, 0.2 $mm^2$ or more may have data locations that are generally evenly distributed over the acquisition time. In some embodiments, local regions having an area of about one-tenth the area of the sample (or 0.05 $mm^2$, 0.1 $mm^2$, 0.2 $mm^2$ or more for a 6 $mm^2$ sample) may have the sample number of data locations taken at times during the first quarter of the acquisition time as during the last quarter of the acquisition time.

Accordingly, motion-corrected high-speed keratometric spectral domain optical coherence tomography (SDOCT) based on a high-speed distributed scan approach may be used such that patient motion, e.g., up to a preset temporal frequency (typically ~100 Hz), appears as low spatial frequency content in the recorded image data. The actual structure of the cornea may be encoded into high spatial frequency content of the recorded image data which is then separated from the motion artifact, e.g., via high-pass spatial filtering. In some embodiments, <1 ms large-angle beam steering may be employed. Accordingly, the OCT scanner 120 may include a non-inertial 2D acousto-optic SDOCT scanner which includes a diffractive optical element for negative chromatic dispersion compensation. However, any suitable OCT scanning technique may be used by the OCT scanner 120. For example, the OCT scanner 120 may employ galvanometers, resonant scanners, rotating polygonal mirrors, MEMS actuated mirrors, rotating prism pairs, or physical movement of the imaging objective.

It should be apparent to one of skill in the art that although embodiments according to the present invention are described with respect to scanning approaches and designs for motion-reduced imaging of the human cornea for the purpose of performing clinically relevant quantitative keratometric measurements, embodiments according to the present invention may be used for the measurement of quantitative morphological features of any object under test instead of or in addition to serial scan imaging techniques, which are subject to measurement artifacts due to motion of the object under test.

In some embodiments, a target accuracy is 0.25D in refractive power measurement, and the measurement of the anterior surface elevation obtained by OCT may be within roughly 40 µm of its actual value, just a few times the full-width at half-maximum (FWHM) resolution of state-of-the-art ophthalmic SDOCT systems.

Two categories of patient motion act to corrupt the accuracy of OCT measurement of anterior corneal surface: axial (defined as parallel to the OCT incident beam) and lateral. Any axial motion during the OCT dataset acquisition contributes directly to accuracy error, whereas lateral motion only contributes as the cosine of the angle between the local corneal surface and the incident OCT beam. Thus, lateral motion may be less important than axial motion by a factor of ~10× at the perimeter of the 3 mm area, a significant factor but not a large enough factor to be completely set aside.

Figure 3:
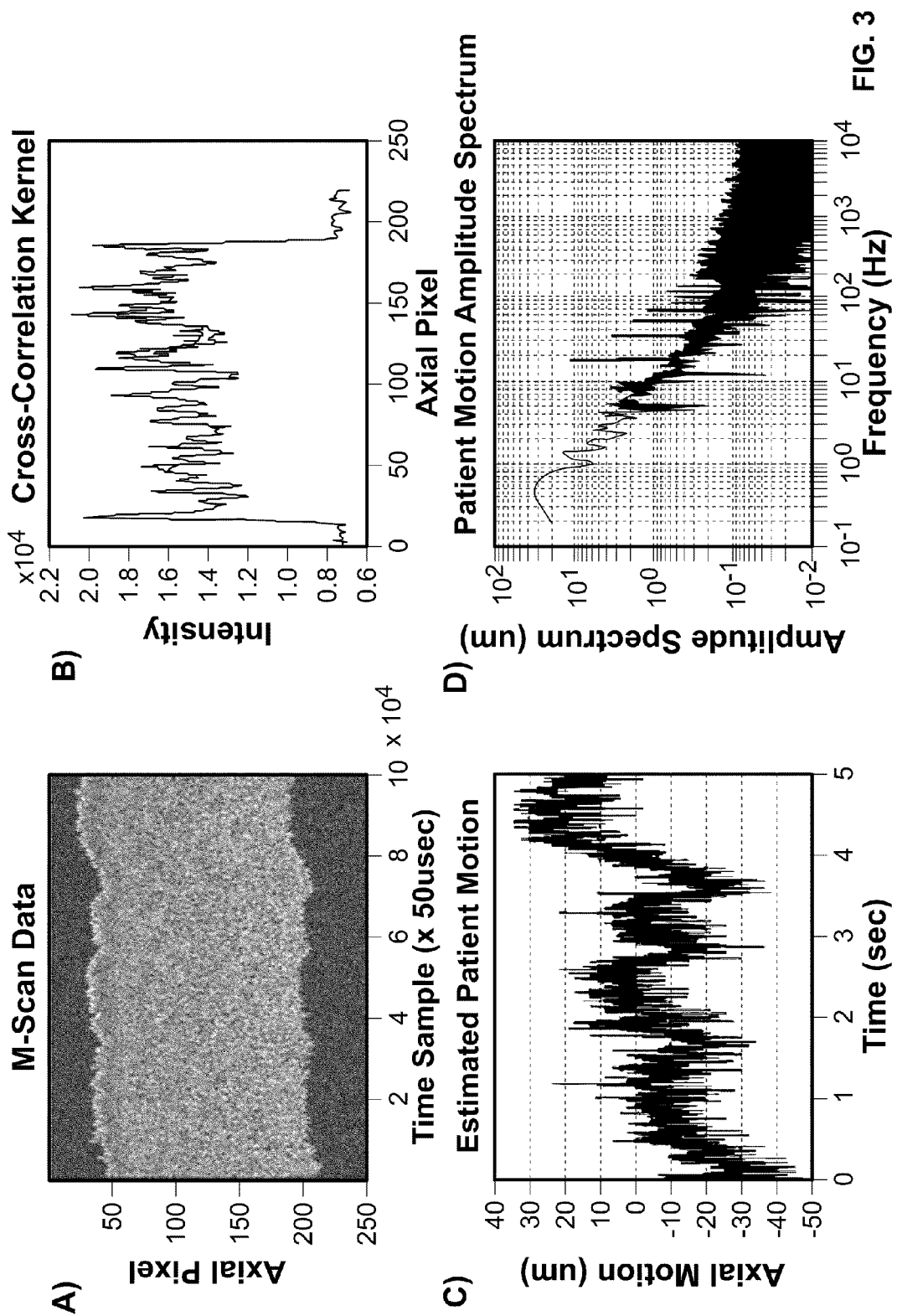
FIGS. 3A-3D are graphs of in vivo corneal axis motion study results.

To obtain an estimate of the magnitude of patient cornea axial translation due to subject motion and its frequency dependence, the amplitude spectrum of axial motion of the cornea of a relaxed, fixated subject with head motion constricted by a forehead rest was measured as described with respect to the data shown in FIG. 3. For this subject averaged over 3 trials, the amplitude of axial motion dropped well below 1 μm for frequencies above ~50-100 Hz. Other patients under less ideal conditions could have variable results, possibly as large as a factor of 10× this frequency. Thus, if the entire corneal measurement could be made within 1-10 ms, the error due to patient motion may be less than the FWHM system axial resolution.

Distributed-Scan Image Acquisition and Motion-Artifact-Reduced Image Reconstruction One approach to make the corneal curvature measurement within the desired time of 1-10 ms would be to take advantage of recent advances in ultra-fast Fourier domain OCT systems, primarily relying upon novel swept-source technologies which have demonstrated A-scan rates up to several hundred kHz. Using these systems, one could potentially acquire all of the corneal data required in 1-10 ms using conventional scanning. However, these systems remain complicated and expensive, are not yet commercially available, and also suffer from the inevitable SNR tradeoff at high speeds limited by shot noise.

Figure 4:
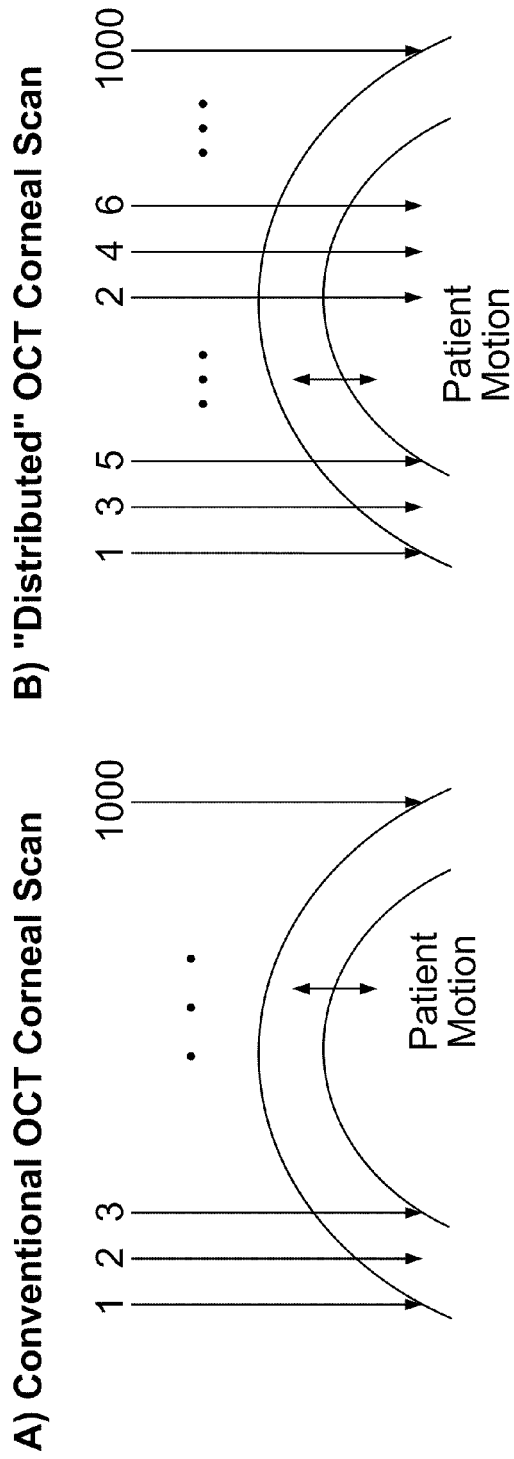
FIG. 4A is a schematic diagram of a conventional SDOCT B-scan acquisition pattern. Patient motion on the scale of tens to hundreds of micrometers may be sufficient to corrupt the refractive power calculation to unacceptable levels.
FIG. 4B is a schematic diagram of a distributed SDOCT acquisition pattern according to some embodiments of the present invention which simulates ultra-high speed scanning by distributing sequential scans across the cornea.

In some embodiments, the B-scan acquisition sequence of even a current-generation 20-50 kHz SDOCT system is modified from the standard sequential scan to a "distributed" scan as illustrated schematically in FIG. 4. If the time delay between each axial scan remains the same, but the distance between sequential scans is extended, this scanning strategy effectively simulates increasing the lateral scan velocity by the ratio between the distributed and sequential scan displacements. For the purpose of eliminating or reducing patient motion artifact, this is equivalent to significantly speeding up image acquisition generally without the linear penalty in image signal-to-noise ratio which would occur for an actual higher velocity scan. Expressed in the frequency domain, the concept is to use a distributed axial scan pattern to shift the spatial frequencies associated with the patient's true corneal shape above the temporal frequencies associated with the patient's motion, such that the motion can be eliminated with a high-pass cut-off filter during image reconstruction. Effectively, the distributed scan pattern modulates the linear scan acquisition at a temporal frequency which can be chosen to be above the predominant frequencies associated with the patient's motion. It should be noted that the particular sequential scan distribution illustrated in FIG. 4 is only one example of many potential scan distributions which could be designed to optimize the lateral distance between sequential A-scans in 2 or 3 dimensions, and which would still fall within the scope of this invention. Also, for 3D objects such as the cornea which are subject to bulk motion, it may be desirable to distribute sequential A-scans widely in both lateral dimensions so as to distribute the A-scans across the entire surface of the cornea. Alternatively, if each B-scan is acquired rapidly compared to the bulk motion of the sample, it may only be necessary to distribute the B-scans rapidly across the sample in a direction orthogonal to the B-scan direction. Many sequential A-scan or B-scan patterns could be designed to optimize the tradeoff between maximizing the distance between sequential scans, staying within the response time of the scanner, and covering the entire corneal surface. A random 1D or 2D distribution of A-scans or B-scans may also be advantageous.

Figure 5:
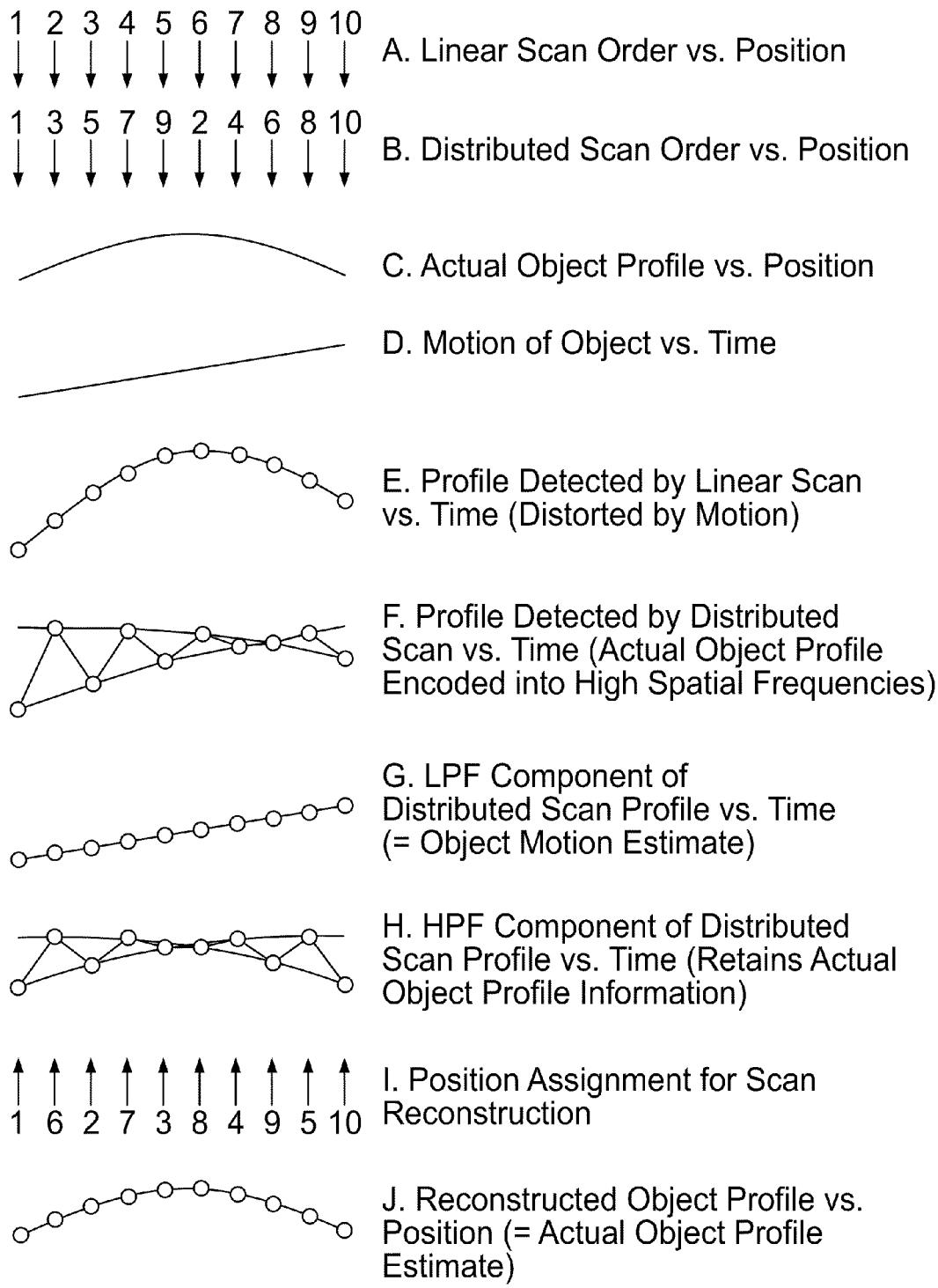
FIG. 5A-5J is a schematic diagram illustrating techniques for estimating a spatial profile of a moving sample using a distributed scan approach according to some embodiments of the present invention.
Figure 6A:
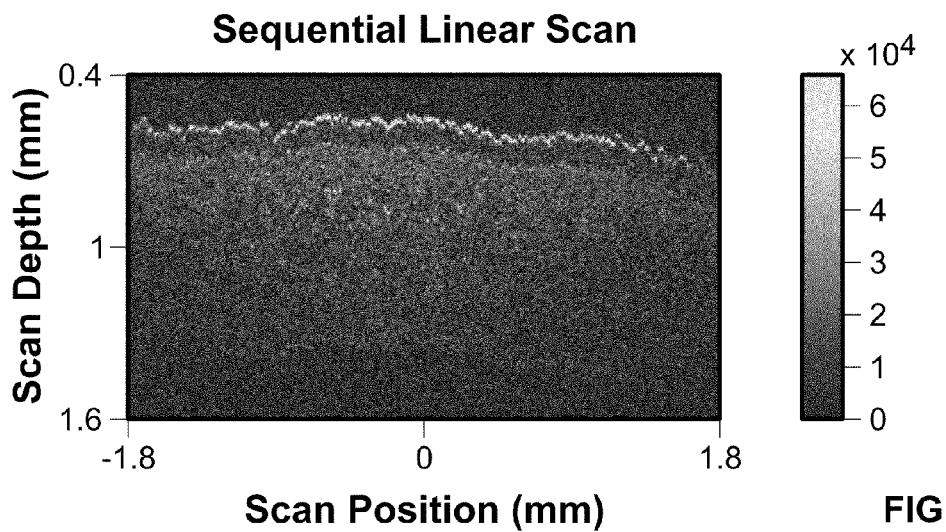
FIGS. 6A-6C are images illustrating a simulation of distributed fast scanning approach for band-limited patient motion rejection. All data was extracted from a sequence of 200 repeated B-scans in the same location, each composed of 600 A-scans (50 µs integration time/A-scan).
Figure 6B:
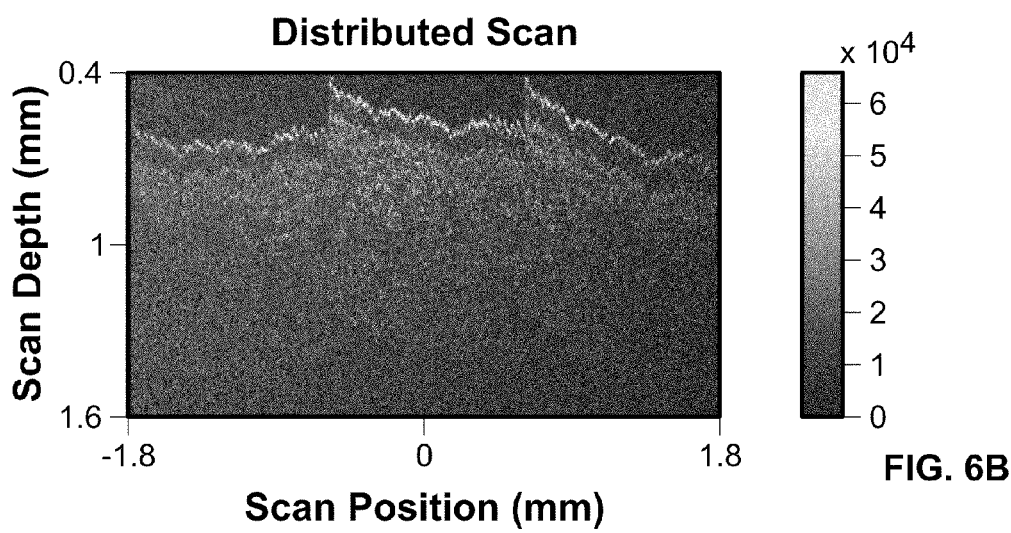
Figure 6C:
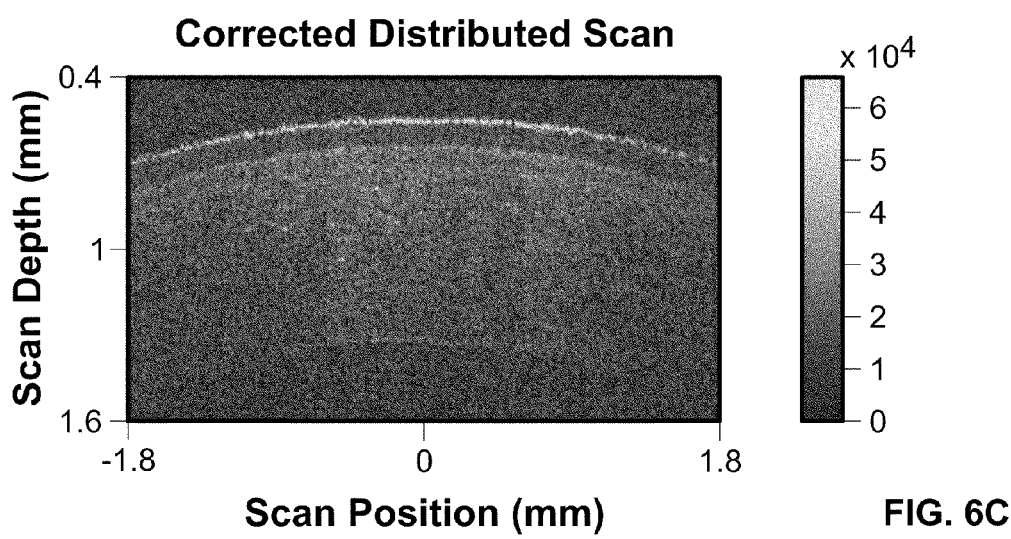

Methods for estimating the profile of a potentially moving object using a distributed scan approach according to some embodiments is illustrated in FIGS. 5A-5J for the simplified case of acquiring only 10 A-scans per B-scan. Assuming that the actual profile of the object is as illustrated in FIG. 5C and the object motion in this simplified case is as illustrated in FIG. 5D, a conventional linear B-scan which records one A-scan in each of the positions indicated in FIG. 5A would observe the significantly distorted view of the object as shown in FIG. 5E. However, acquiring the same 10 A-scans in the distributed scan pattern illustrated in FIG. 5B will encode the true object profile into high spatial frequencies as illustrated in FIG. 5F. Following acquisition of the distributed scan profile, the next method step for a real object under test is to estimate the actual profile of the object observed by the distributed scan. For an object with an obvious bright surface or some other prominent feature of known profile, this can be done by detecting that feature using a thresholding or related image processing operation, and then comparing the observed profile of the prominent feature to the known profile of the prominent feature. If the object does not contain a prominent feature of known surface profile, the apparent profile of the object may be estimated from the location of the peak of the normalized cross-correlation between adjacent A-scans. E. A. Swanson, J. A. Izatt, M. R. Hee, D. Huang, C. P. Lin, J. S. Schuman, C. A. Puliafito, and J. G. Fujimoto, Optics Letters 18:1864-1866, 1993. Once the apparent profile of the object under distributed scanning is obtained, it contains information about the motion of the object during the acquisition in the lower spatial frequencies and information about the true shape of the object in the higher spatial frequencies. If these spatial frequencies are well separated, a cutoff frequency can be chosen which is above the assumed band-limited temporal frequencies of the motion but which still preserves most of the spatial frequencies describing the object's true profile. The LPF components of the observed profile then contain an estimate of the motion of the object, while the HPF still retain all but the lowest spatial frequency information about the object's true profile as illustrated in FIG. 5G-H. To recover an image of the true object structure, a motion-artifact-free B-scan may be reconstructed from the distributed scan data by re-assigning the A-scans acquired in a distributed manner back to their correct spatial positions in the image as shown in FIG. 5I. Since this re-assignment just amounts to undoing the original scan distribution, the correct re-assignment positions simply correspond to the A-scan location in FIG. 5A corresponding to the A-scan number denoted in FIG. 5B.

The distributed scanning approach is further illustrated for a 1D scanning case using simulated data from a commercial corneal SDOCT scanner as illustrated in FIGS. 5A-5H. To extend this approach to 3D, it is assumed that each B-scan is acquired within the ~10 ms limit (i.e., 200 A-scan images acquired with 50 μs integration time) and thus contains no motion artifact. Sequential B-scans, however, do contain motion artifacts which can be mitigated by distributing the B-scan acquisition across the corneal surface and using the spatial filtering and reconstruction approach described in FIG. 5.

The distributed scan approach applies to both radial and raster scanning, and is also extensible to fast scan distribution in both axes for axial motion rejection.

Fast Broadband OCT Scanner Design

Other scanning techniques utilized for OCT involve minor angular movement (i.e. galvanometers, resonant scanners, rotating polygonal mirrors, MEMS actuated mirrors), rotating prism pairs, or physical movement of the imaging objective. All of these techniques work for sequential scanning in the image plane. In some embodiments, these scanning techniques, as well as acousto-optic deflectors, may be used for non-sequential, distributed scanning patterns according to embodiments of the present invention.

Acousto-optic deflectors have previously been commercially developed to scan (deflect) monochromatic light over finite scan angles. The exact deflection angle is linearly dependent on the wavelength of light, previously preventing the use of light sources with 10 s of nanometers of bandwidth.

Figure 7A:
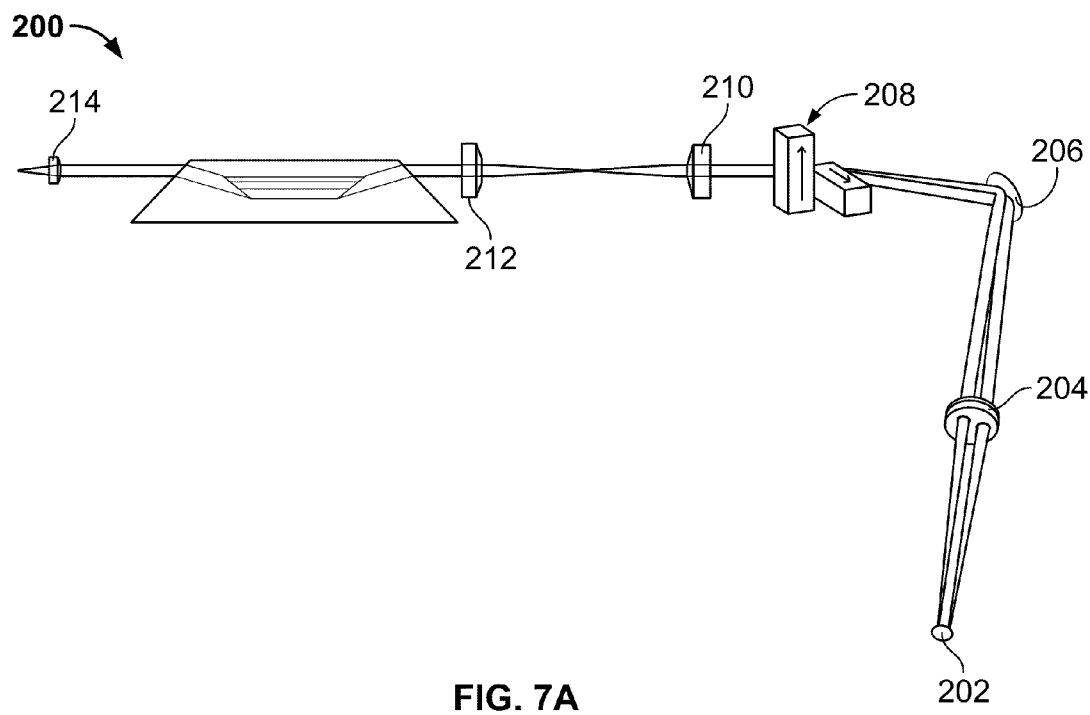
FIGS. 7A-7B illustrate two optical designs utilizing acousto-optic deflectors for OCT sample arm optics according to some embodiments of the present invention
Figure 7B:
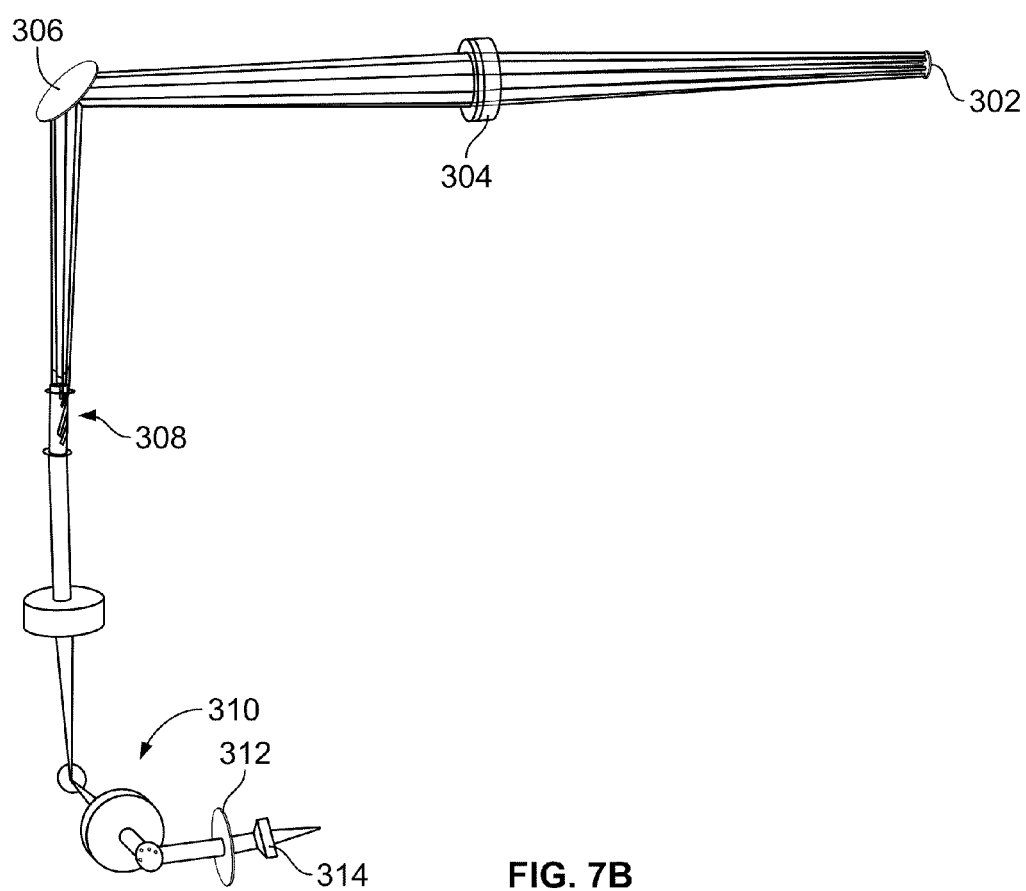

For distributed SDOCT sample arm scanning, a scanning approach based on acousto-optic scanners may be used which allows for random-access scanning on the order of 10 μs. A ZEMAX ray diagram illustrating two fast-scanning OCT sample arms including the scanning optics are illustrated in FIGS. 7A-7B. As illustrated in FIG. 7A, a sample arm 200 of an OCT device configured to scan a sample 202 includes a diffractive refractive hybrid lens 204, a prism 206, acousto-optic deflectors (AOD) 208, lenses 210, 212 and a collimating lens 214. The AODs 208 are configured to control the position of the sample beam on the sample 202, e.g., using a scanning pattern as described herein. As shown in FIG. 7B, another sample arm 300 of an OCT device is configured to scan a sample 302. The sample arm 300 includes a diffractive-refractive hybrid lens (DFHL) 304, a folding mirror (FM) 306, acousto optic-deflectors (AOD) 308, an optical relay (OR) 310, a diffraction grating (DG) 312, and a collimating lens (CL) 314. The AODs 308 are configured to control a beam scan by controlling the position of the sample beam on the sample 302, e.g., using a scanning pattern as described herein. It should be understood that any suitable OCT device and/or scanning arm may be used to collect data according to scanning patterns described herein.

In particular, acousto-optic deflectors (AOD) have been used previously in a variety of applications including multiphoton laser-scanning microscopy (MPLSM) as a non-inertial scanning technique; however these systems are typically limited in optical bandwidth to ~15 nm. The developed solution in MPLSM is to use negative angular dispersion prior to the AOD pair. R. Salomé, Y. Kremer, S. Dieudonné, J.F. Léger, O. Krichevsky, C. Wyart, D. Chatenay, and L. Bourdieu, J. Neuroscience Methods, 2006, 154(1-2), 161-174. An AOD can be modeled as a diffraction grating with a time-varying ruling $$\left(\Lambda = \frac{2v_s}{f_c}\right).$$

If designed to correspond to $\sqrt{2}*f_c$ where $f_c$ is the center acoustic frequency, this can fully correct the center scan position and mostly correct all other positions. This technique is successful in MPLSM, correcting the limited 15 nm of bandwidth of the femto-second laser to an acceptable degree.

The OCT scanning systems illustrated in FIGS. 7A-7B use an AOD pair (208, 308) with 9 mm aperture and 2.7° scan angle illuminated by a light source with center wavelength of 828 nm and a 68 nm bandwidth. The effects of this bandwidth can be seen in the ZEMAX spot diagram in Panel A in the top of FIGS. 8A-8D, where the uncorrected spectrum is unacceptably dispersed to 100's of microns at the cornea for a given spot. FIG. 8D shows spots at the cornea with the addition of a diffraction grating prior to the AOD pair. Spatial dispersion is still present causing spots at the edge to have a length of about 200 μm.

Figure 8A:
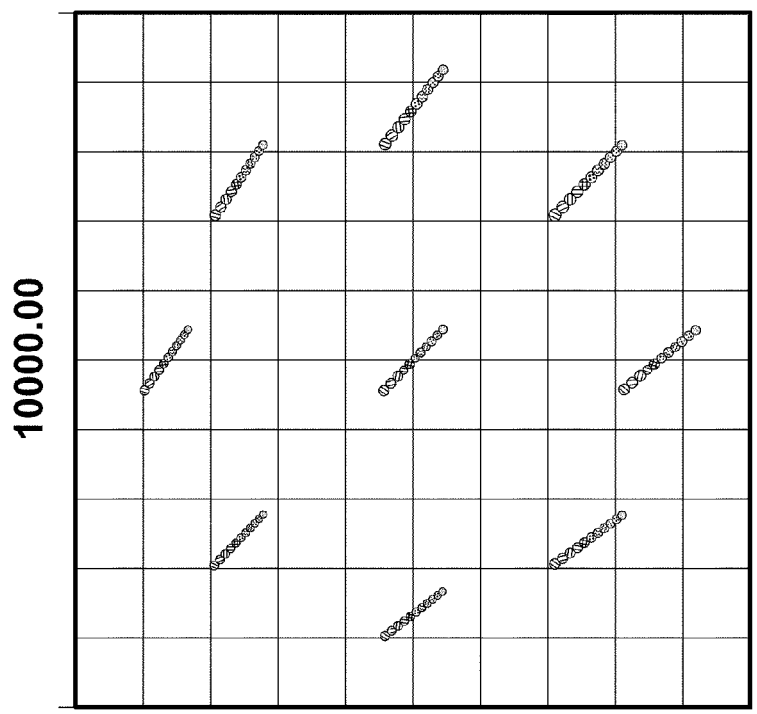
FIG. 8A-8C is a ZEMAX spot diagram on a cornea using an AOD without any spatial dispersion correction (FIG. 8A), a spot diagram on the cornea with spatial dispersion correction provided by a diffraction grating prior to the OAD (FIG. 8B) and a spot diagram on the cornea with a total spatial dispersion correction using both diffraction grating before and DRHL after the AOD showing ±3.5 mm radial scan range (FIG. 8C). The scale bars show 10 mm square on all three spot diagrams.
Figure 8B:
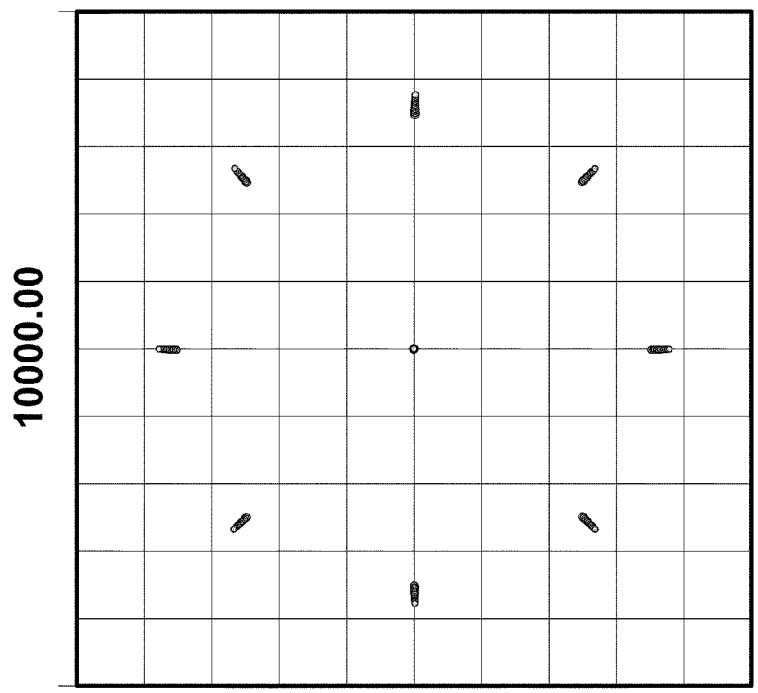
Figure 8C:
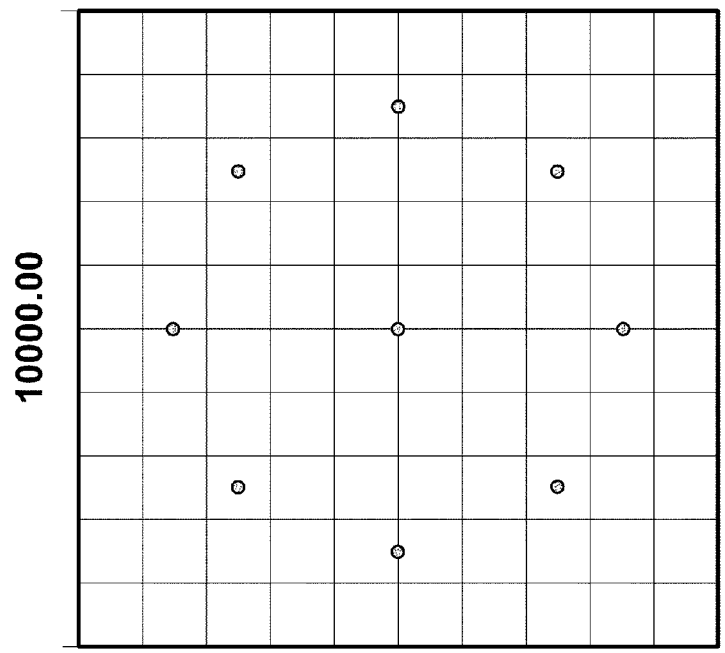
Figure 8D:
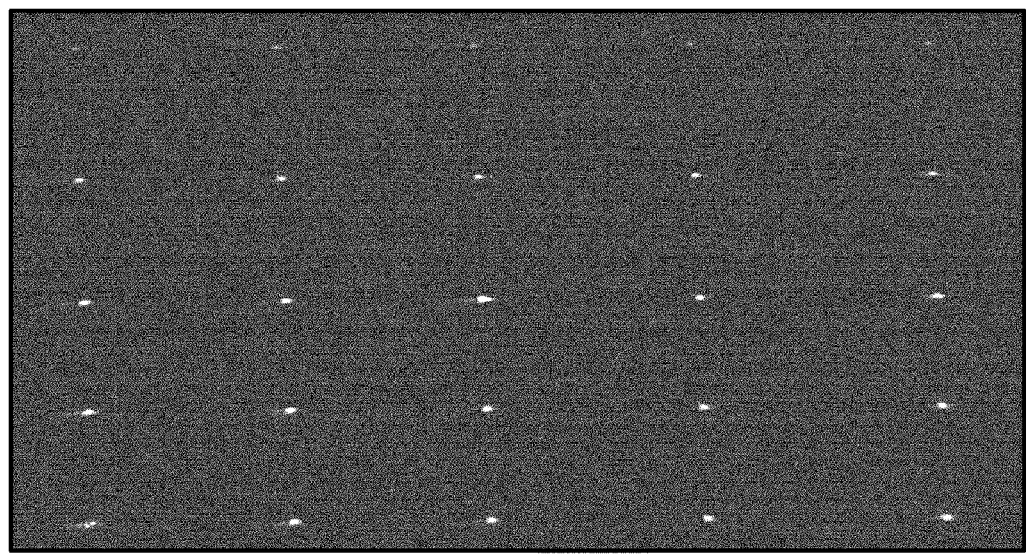
FIG. 8D is a diagram illustrating experimental results showing a 5×5 mm grid using the scan pattern of FIG. 4B.
Figure 9A:
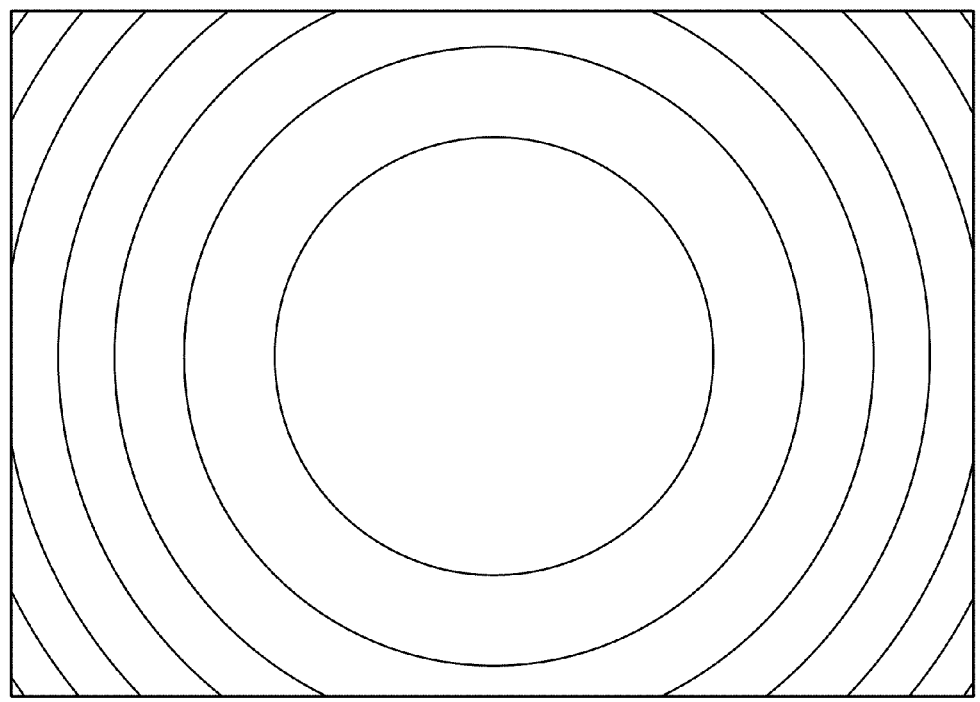
FIG. 9A is an intensity image of a center of a diffractive optic illustrating Fresnel zones. The image is 2.88 mm by 2.16 mm.
Figure 9B:
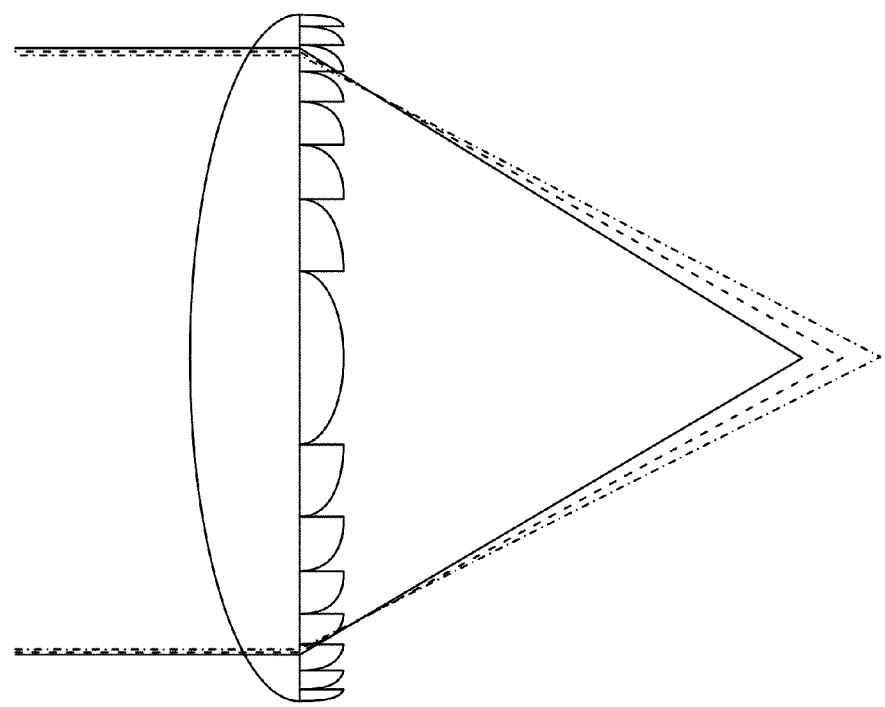
FIG. 9B is a diagram of a diffractive-refractive hybrid lens illustrating a negative chromatic dispersion.

The difference in spatial dispersion structure can be seen between FIGS. 8A-8C, with FIG. 8D showing an axially symmetric structure. Noticeably, lower wavelengths are closer to the center of the scan range with longer wavelengths farther out. A similar dispersion structure can be seen in the effects of positive chromatic aberration of a glass singlet lens. To further correct the spatial dispersion caused by the AOD pair, a diffractive-refractive hybrid lens (DRHL) is incorporated (e.g., the DRHL 304 illustrated in FIG. 7B). Such a lens is unique in that it exhibits negative chromatic aberration as illustrated in FIG. 9B. The DRHL includes two elements: a glass singlet made of BK7 and an axially symmetric diffractive optic (manufactured by Apollo Optical Systems). The singlet provides some of the optical power and also acts as protection for the diffractive optic. The diffractive optic is acrylic that has been diamond turned with Fresnel zones as small as 10 μm in width. An intensity image of the diffractive optic can be seen in FIGS. 9A, highlighting the center of the lens as well as several of the associated Fresnel zones. It is highly chromatically dispersive however it corresponds to a negative Abbe number, whereas glasses and other refractive materials have a positive Abbe number. Using the DRHL after the AOD in place of a standard refractive lens, the dispersion from the AOD is fully corrected as seen in FIG. 8C. Using this design, the OCT scanning spots are corrected across the full 7 mm lateral scan range with a spot size under 29 μm FWHM at each point over a 7 mm scan range.

Figure 10:
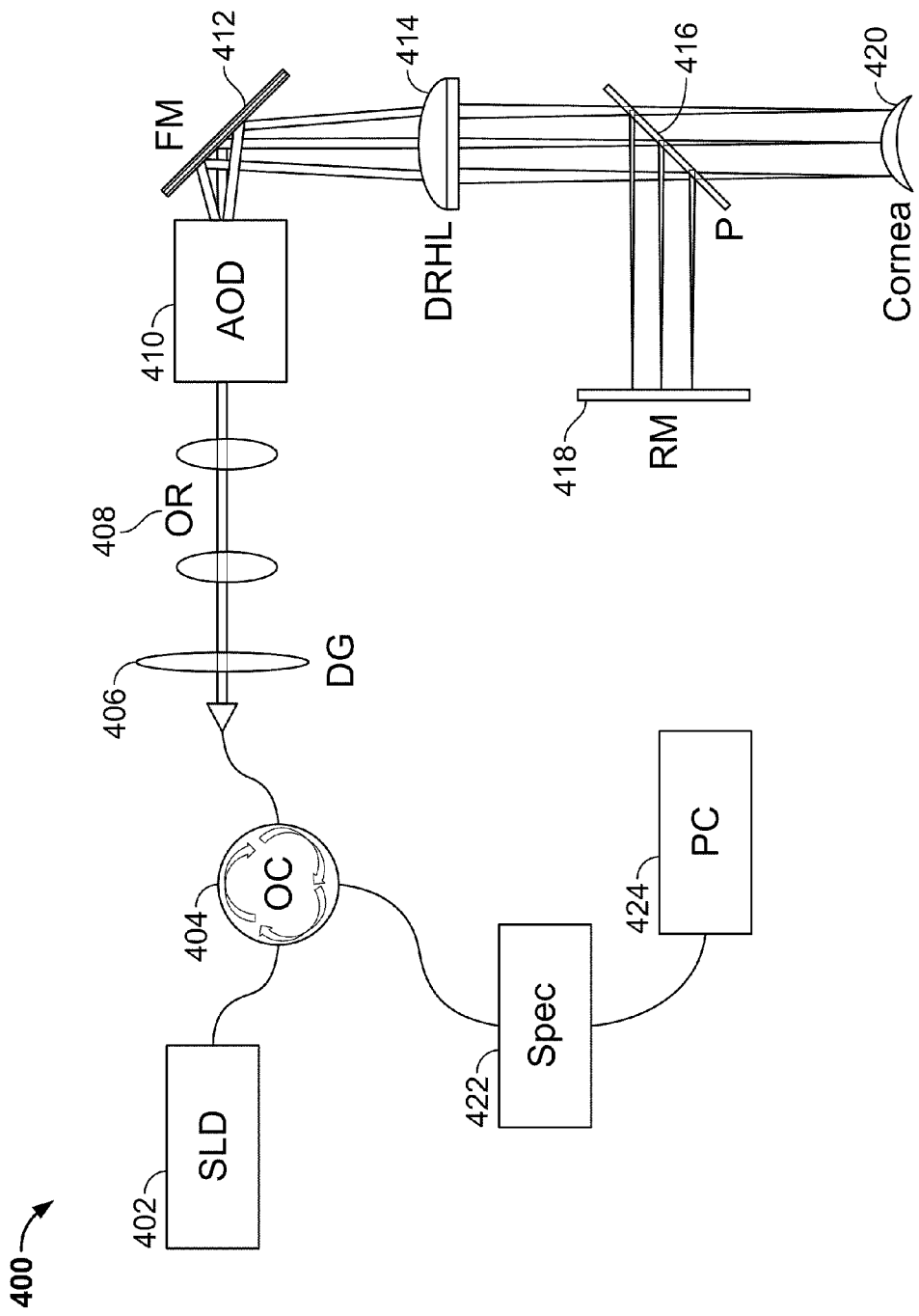
FIG. 10 is a schematic diagram of an OCT system according to some embodiments of the present invention. SLD—Superluminescent Diode; OC—Fiber-Based Optical Circulator; DG—Diffraction Grating; OR—Optical Relay; AOD—Acousto-optic Deflector; FM—Folding Mirror; DRHL—Diffractive-Refractive Hybrid Lens; P—8% Reflective and 92% Transmissive Pellicle Beam Splitter; RM—Reference Mirror; Cornea—Patient's Cornea; Spec—Spectrometer; PC—Acquisition and Control Computer.

An example design of a full SD-OCT system 400 can be seen in FIG. 10. The SD-OCT system 400 includes an illumination source or superluminescent diode 402, an optical circuolor 404, a diffraction grating 406, an optical relay 408 with relay lenses 408A, 408B, an acousto-optic deflector 410, a folding mirror 412, a diffractive refractive hybrid lens 414, a beam splitter 416 configured to direct a portion of light to a sample 420, a reference mirror 418, a spectrometer 422, and an acquisition and control computer 424. The control computer 424 may be configured as illustrated in the system 100 shown in FIG. 1 to control a beam scan as described herein. Two design choices are noted. The first is the integration of the reference and sample arms. Although in some embodiments, the reference and sample arms are not integrated, an integration of the reference and sample arms may have the benefit of providing integrated optical path length dispersion matching between both arms. This design is not typically chosen due to both the sample and the reference arm being scanned adding a layer of complexity. This is tradeoff may be required, however, due to the oscillating optical path change induced by the AOD pair 410. The RF frequency of the AODs 410 is in the 10 s of MHz causing the path length of the beam to oscillate by a fraction of a wavelength at that same frequency. Because both the sample and reference arms pass through the AODs 410, this effect is canceled out. A second design choice is the use of a circulator 404 in place of a 2-by-2 fiber coupler; however, it should be understood that in some embodiments, a 2-by-2 fiber coupler may be used. Having both the sample and reference arm in the same path, negates the need for two fiber ports allowing for a higher signal throughput from the sample. The use of a circulator 404 also negates the need for a separate optical isolator on the SLD 402.

Figure 11A:
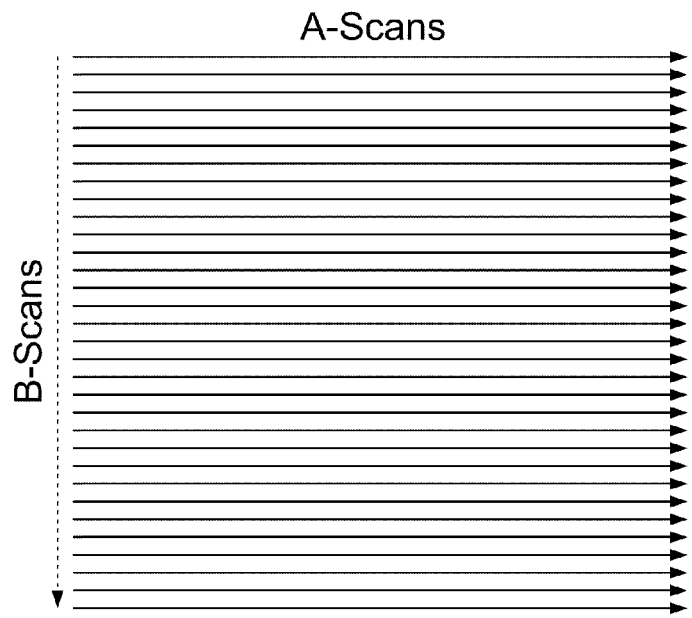
FIG. 11A is a diagram of a raster scan according to some embodiments of the present invention in which the scanning beam begins in the upper left, scans left to right and then down after each line is complete.
Figure 11B:
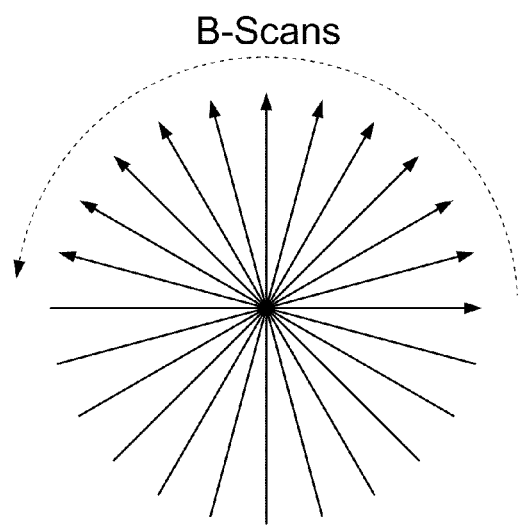
FIG. 11B is a diagram of a radial scan with all B-scans equally angularly spaced, passing through the apex of the cornea.
Figure 11C:
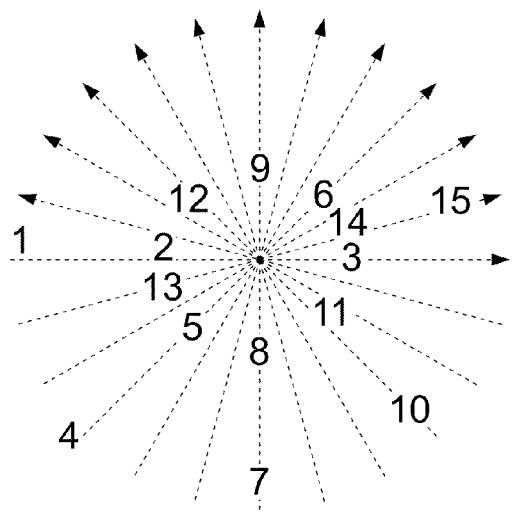
FIG. 11C is a diagram of a distributed radial scan according to some embodiments of the present invention where each number corresponds to spatial location of each temporally sequential A-scan. While the diagram only shows 15 A-scans, it should be understood that this design can be extrapolated to cover the same spatial locations as the radial scan, e.g., of FIG. 11A.
Figure 11D:
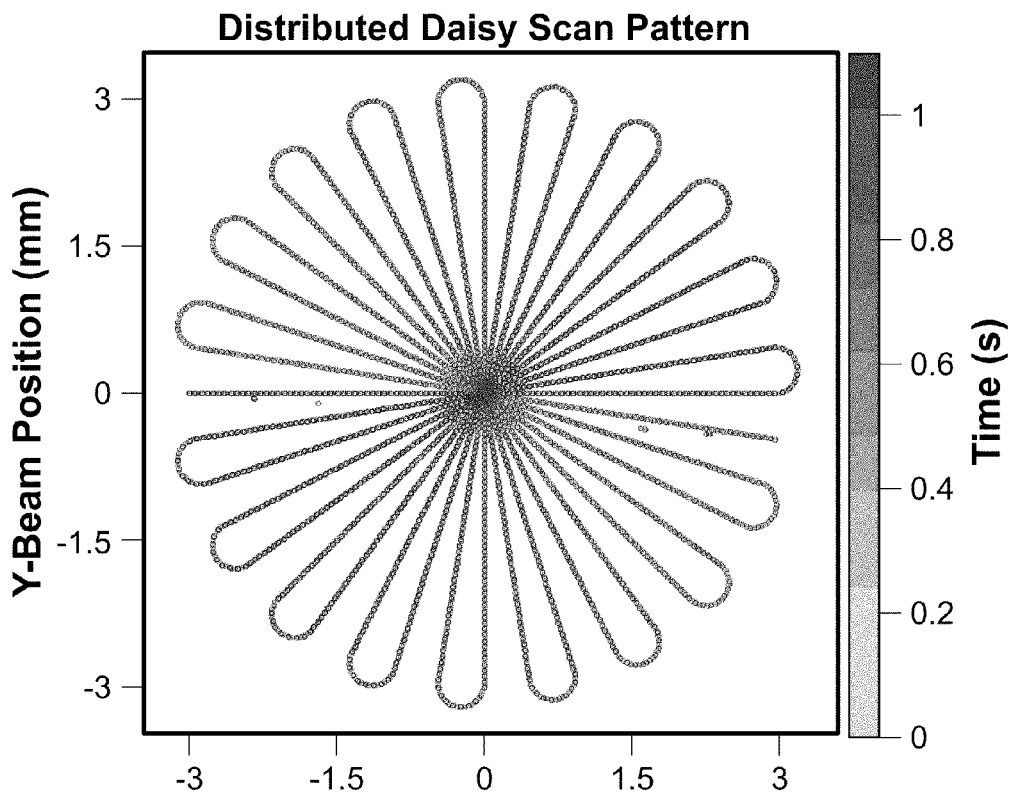
FIG. 11D is a diagram of a "daisy scan" pattern that may be used in which a generally continuous scanning beam is used according to some embodiments.
Figure 11E:
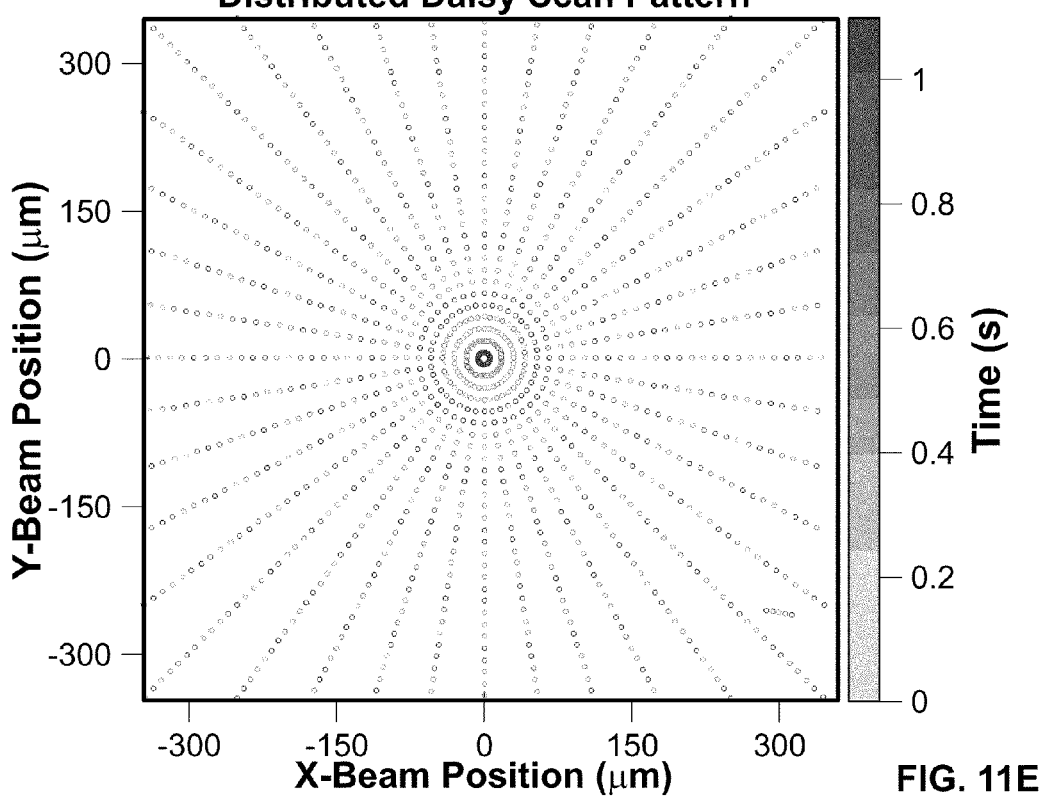
FIG. 11E is a diagram of the spatially non-sequential data acquisition pattern according to some embodiments.

Scan patterns play an important role in accurate keratometric measurements using SD-OCT. A typical raster scan will yield high reflectivity at the apex of the cornea, generally yielding quality images; at the beginning and end of the scan, near the edges of the cornea, reflectivity will be low creating datasets that are difficult to measure. The scan pattern can be seen in FIG. 11A. A radial scan consists of B-scans that are taken through the apex at each multiple of angle theta. This has the advantage of having a high image quality at the center of each B-scan though lacking at the edges. In addition the apex of the cornea is oversampled while the outer edges are under sampled. This pattern can be seen in FIG. 11B. Both of these techniques though suffer from slow scan time. The temporal correlation between distant points is low while it is quite high locally. Switching to a distributed scan pattern shifts the patient motion that occurs during acquisition to higher spatial frequencies. Local points are no longer temporally correlated and only spatially. In this way the patient motion is averaged over the entire image and can later be filtered out. FIG. 11C shows a radial scan adapted to a distributed scan pattern. In some embodiments as illustrated in FIG. 11D, a "daisy scan" pattern may be used in which a generally continuous scanning beam is used; however the resulting data acquisition pattern may be spatially non-sequential as shown in FIG. 11E. The scanning patterns shown in FIGS. 11D-11E may be acquired using generally continuous scanning, for example, with galvonometric scanning.

Figure 12:
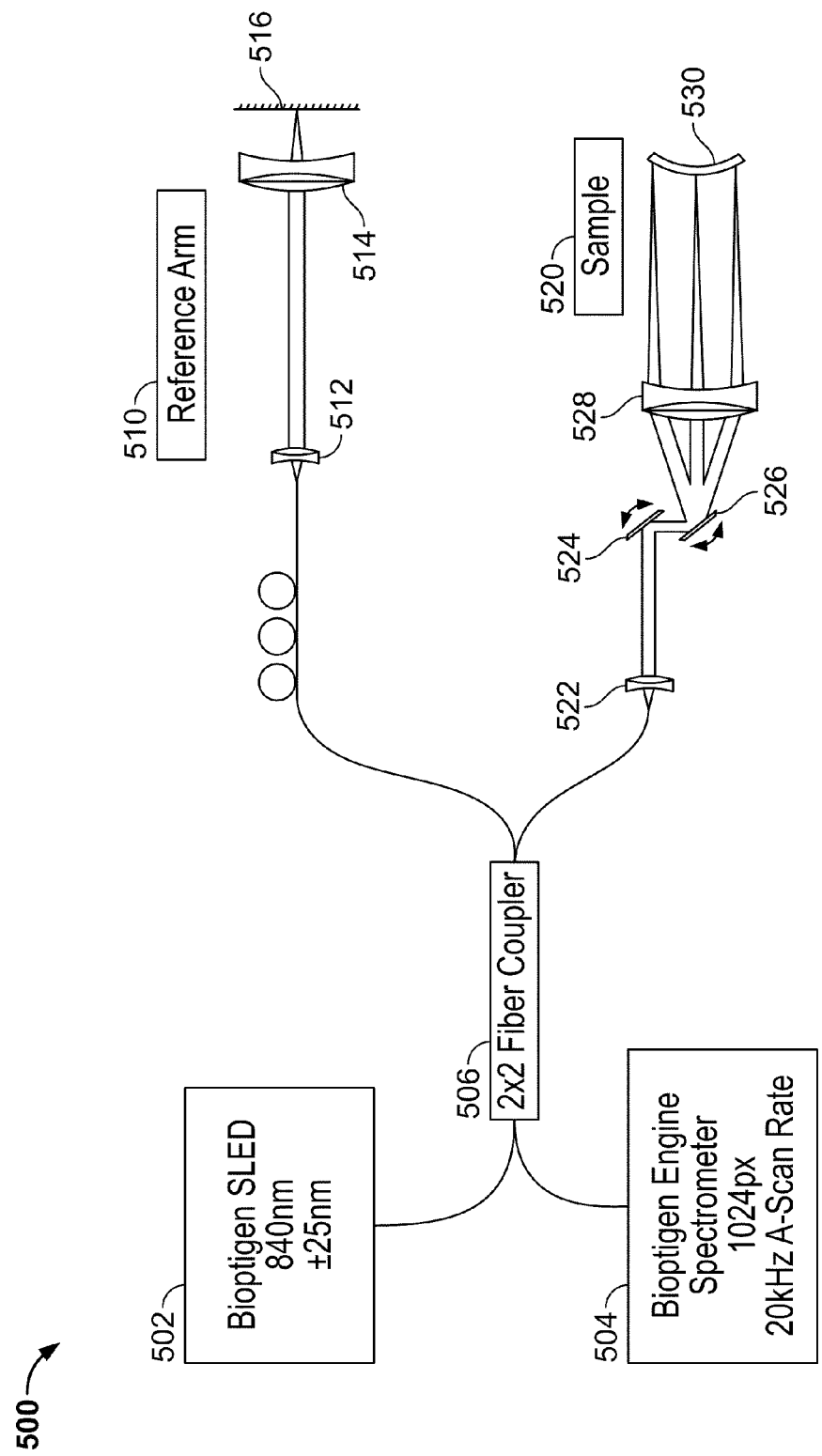
FIG. 12 is a schematic diagram of an OCT system according to some embodiments of the present invention. The system uses a source with a center wavelength of 840 nm and a bandwidth of 50 nm. Light is coupled to the sample and reference arms using a 2×2 fiber coupler and the mixed light is detected with a high-speed spectrometer. The spectrometer detector consists of a 1024-pixel line-scan camera operated at up to a 20 kHz line rate.

Methods using a commercial Spectral Domain Optical Coherence Tomography (SDOCT) system (Bioptigen, Inc.) have been developed which allows for distributed scanning across a volume using conventional galvonometric scanning. A schematic diagram of the SDOCT system 500 used is illustrated in FIG. 12. The SDOCT system 500 includes a light source 502, a spectrometer 504, a fiber coupler 506 (such as a 2×2 fiber coupler), a reference arm 510 and a sample arm 520. The reference arm 510 includes optics 512, 514 and a reference mirror 516. The light source 502 is a superluminescent diode with a center wavelength of 840 nm and a bandwidth of 49 nm; however, any suitable light source may be used. The measured SNR was 105 dB at a line rate of 20 kHz. Sample arm light is delivered to the eye via a single mode fiber, e.g., to a handheld scanner or other scanner containing the sample arm 520 for scanning a sample 530. The sample arm 520 includes collimating optics 522 for the light exiting the fiber, a pair of orthogonal galvonometric mirrors 524, 526 for two dimensional scanning, and a lens 528 that was designed to have a telecentric output. In this example, a portable telecentric scanner including the sample arm 520 was mounted on a modified slit-lamp base with a chin and forehead rest for subject stability. Reference and sample arm light interfere on a high speed line camera at the output of a high-throughput spectrometer developed and built by Bioptigen, Inc. Software provided by Bioptigen, Inc. is used for real-time data detection, processing, display, and archiving while custom software was used for beam scanning control.

Figure 13:
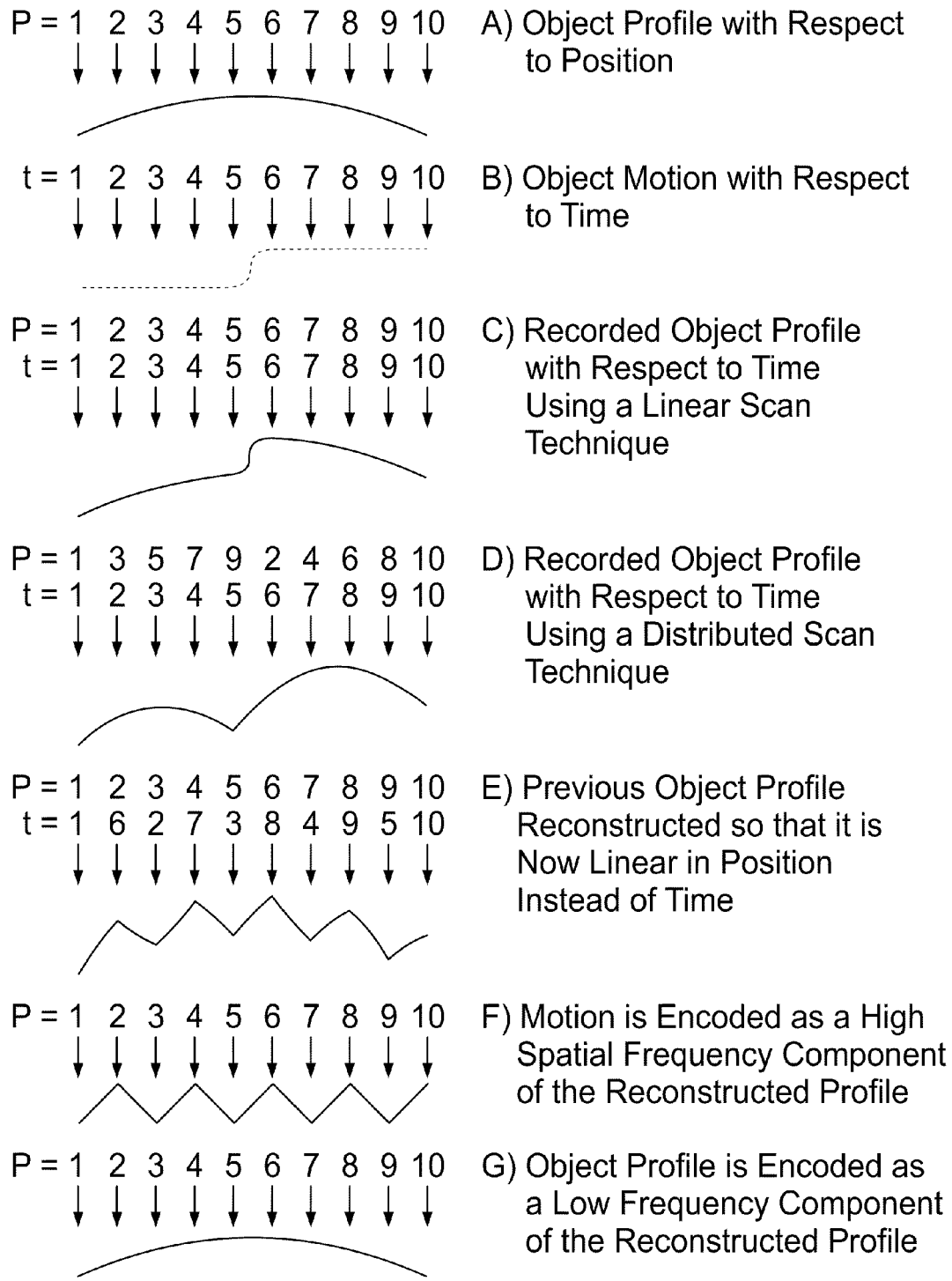
FIG. 13 is a schematic diagram illustrating exemplary distributed scanning using a single B-scan as a model according to some embodiments of the present invention. During the acquisition, the object moves suddenly. This would appear as an artifact using a linear scan technique and would prohibit accurate measurement of corneal refractive power. Using a distributed scanning technique, spatially adjacent points are decorrelated temporally. By applying the proper reconstruction, the object motion is encoded as a high frequency spatial component. By applying a low pass filter, the original object profile can be recovered.

In a conventional SDOCT linear scan of an object, sequential A-scans are both temporally and spatially related. Using a distributed scanning technique, however, spatially adjacent points are temporally decorrelated. By applying the proper reconstruction, the object motion is encoded as a high frequency spatial component. By applying a low pass filter, the original object profile can be recovered. The techniques for applying a low pass filter are illustrated in FIG. 13.

A custom waveform in a radial scan pattern in which the radial scan lines are non-sequentially obtained was applied to the galvonometers that was a continuous motion but at the same time provides a distribution of scan points on a single radial path over time. The key point for this scan pattern is that two spatially adjacent points are not acquired on the same pass over a radial path. In this way two points can be spatially correlated but not temporally correlated. This particular custom waveform yielded a 512×500×20 voxel volume that was radially symmetric though this pattern could be extended to having more or less radial sections or points within a section. For example, the lateral scan diameter was designed to be 6 mm and the axial depth was ~2 mm. An integration time of 100 µs per line was chosen as a compromise between having a scan time per pass that was fast enough to ignore patient motion during a single pass, slow enough to allow the galvanometers to operate at a safe speed, and having enough SNR to segment both the anterior and posterior of a cornea. The daisy scan pattern shown below in FIG. 11D, yields 5 passes across 20 separate radial paths. This creates 100 corneal profiles, one for each pass across the 20 paths. In a conventional radial scan pattern, the time between acquisitions for two spatially adjacent points is on the order of the integration time of the camera (in this case 100 µs). By using a scan pattern similar to the one proposed the time between acquisitions for the same two points can be as much larger, in the above case on the order of 1 second.

Figure 14:
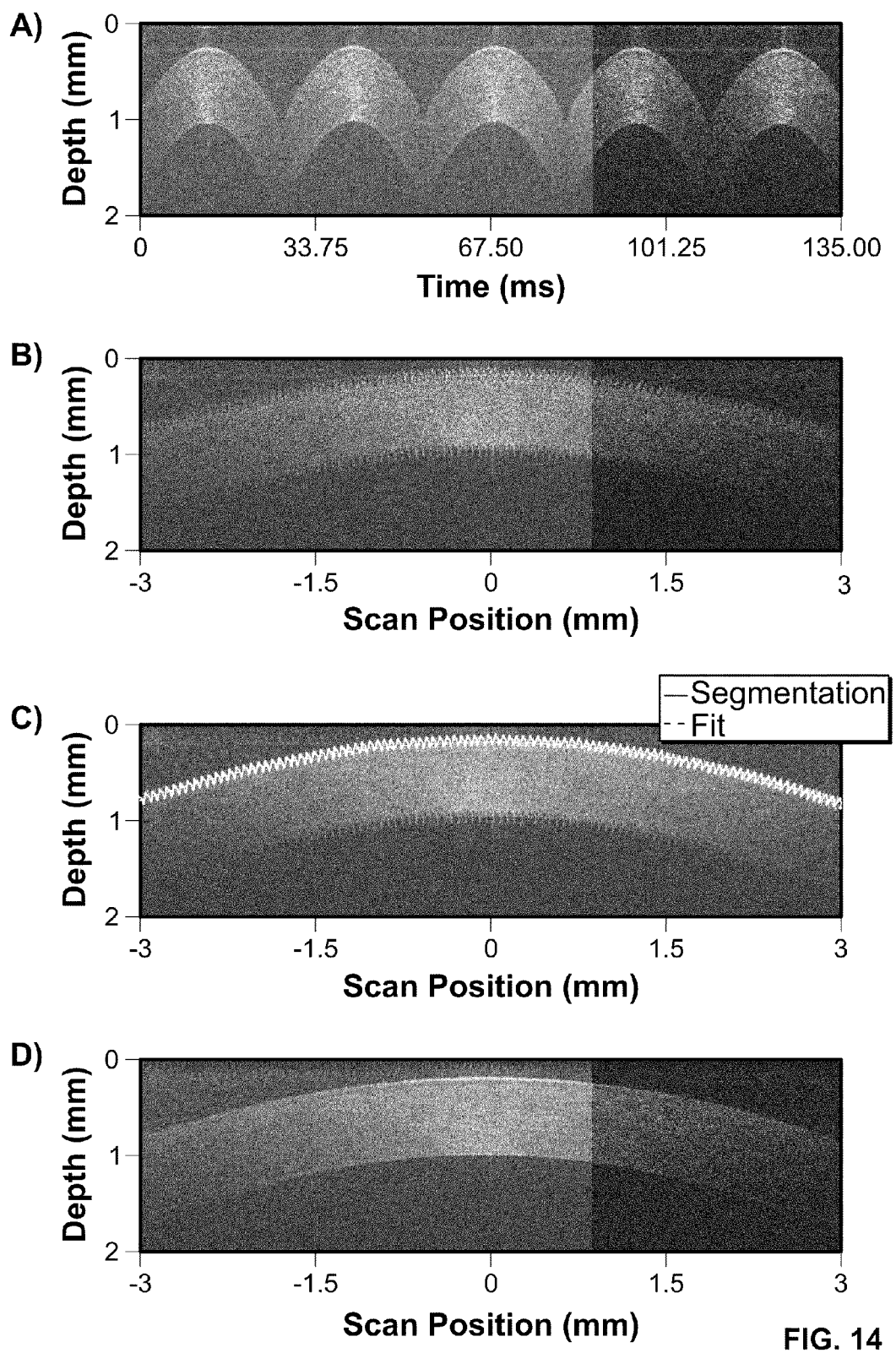
FIG. 14A is an image illustrating the first 540 lines of data acquired from the distributed scan pattern. Each small corneal profile contains 100 lines of data from 5 different radial slices. Integration time for this acquisition was 250 µs per A-scan.
FIG. 14B is an image illustrating the distributed-scan data reconstructed so that all A-scans were returned to their correct spatial position.
FIG. 14C is an image illustrating the corneal epithelium automatically segmented as highlighted. The resulting surface data was fit with a $5^{th}$-order polynomial to act as a low pass filter.
FIG. 14D is an image in which the vertical difference between the segmentation and the fit was applied locally to return each A-scan to its correct axial location, generating the final fully sampled, motion-corrected B-scan.

Each A-Scan acquired had DC subtraction, dispersion compensation and FFT applied in real-time during acquisition (FIG. 14A). Because the A-scans were acquired linear in time but not in space, in post-processing each A-scan was moved to its correct spatial location, while inactive lines from the original data were removed to create a reconstructed B-scan (FIG. 14B). The position of the epithelium in each B-scan was found using a semi-automated segmentation algorithm. The axial position information corresponding to each A-scan within each B-scan was obtained by applying a low pass spatial filter. In this example the low pass filter was provided by a 5th order polynomial that was fit to the axial position information. By removing the difference between the fit and the recorded axial position of each A-scan filters out the high-spatial-frequency of the patient motion. In this way each A-scan was translated axially to its correct position.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of reducing motion artifacts in Optical Coherence Tomography (OCT), the method comprising:
    scanning a sample with a scan pattern to acquire OCT data at a plurality of data locations, the data locations being distributed in the scan pattern across the sample such that at least some spatially adjacent data locations are acquired non-sequentially in time; and estimating at least one spatial profile of the sample corresponding to a sample surface or an aspect of an internal structure of the sample responsive to the OCT data.

2. The method of claim 1, wherein scanning the sample comprises:
scanning the sample with a series of scanning lines such that at least one of the series of scanning lines is between two previously acquired scanning lines.

3. The method of claim 2, wherein the series of scanning lines comprises a raster scan such that each of the series of scanning lines comprises a series of generally parallel scan lines, and at least one of the series of generally parallel scanning lines is between two previously acquired scanning lines.

4. The method of claim 2, wherein the series of scanning lines comprises a series of radial scanning lines, beginning locations of the series of radial scanning lines define a generally circular shape, and the at least one of the series of scanning lines that is between two previously acquired scanning positions comprises at least one radial scanning line having a beginning location that is between a beginning location of two previously acquired scanning lines along the generally circular shape of beginning locations of the series of radial scanning lines.

5. The method of claim 1, wherein estimating a profile comprises estimating a location of a peak of a normalized cross-correlation between spatially adjacent scans.

6. The method of claim 1, wherein estimating a profile comprises ordering the OCT data in a spatial order.

7. The method of claim 1, wherein the OCT data is acquired in an ocular region having an diameter of about 6 mm during an acquisition time, and the data locations are temporally distributed so that a selected region having an area of about 0.2 mm$^2$ includes a subset of the plurality of data locations that is generally evenly distributed over the acquisition time.

8. The method of claim 1, wherein the OCT data is acquired in an area of the sample during an acquisition time, and the data locations are temporally distributed so that a selected region of the sample having an area of about one-tenth the area of sample includes a subset of the plurality of data locations that is generally evenly distributed over the acquisition time.

9. The method of claim 1, wherein the OCT data is acquired in an ocular region having a diameter of about 6 mm during an acquisition time, and the data locations are temporally distributed so that a selected region having an area of about 0.2 mm$^2$ includes a subset of the plurality of data locations that includes a number of data locations acquired during a first quarter of the acquisition time that is generally equal to a number of data locations acquired during a last quarter of the acquisition time.

10. The method of claim 1, wherein the OCT data is acquired in an area of the sample during an acquisition time, and the data locations are temporally distributed so that a selected region of the sample having an area of about one-tenth the area of sample includes a subset of the plurality of data locations that includes a number of data locations acquired during a first quarter of the acquisition time that is generally equal to a number of data locations acquired during a last quarter of the acquisition time.

11. An Optical Coherence Tomography (OCT) system comprising:
an OCT scanner configured to scan a sample with a scan pattern to acquire OCT data at a plurality of data locations, the data locations being distributed in the scan pattern across the sample such that at least some spatially adjacent data locations are acquired non-sequentially in time; and a profile estimation module configured to estimate a profile of the sample corresponding to a sample surface or an aspect of an internal structure of the sample responsive the OCT data.

12. The system of claim 11, wherein the OCT scanner is configured to scan the sample by scanning the sample with a series of scanning lines such that at least one of the series of scanning lines is between two previously acquired scanning lines.

13. The system of claim 12, wherein the series of scanning lines comprises a raster scan such that each of the series of scanning lines comprises a series of generally parallel scan lines, and at least one of the series of generally parallel scanning lines is between two previously acquired scanning lines.

14. The system of claim 12, wherein the series of scanning lines comprises a series of radial scanning lines, beginning locations of the series of radial scanning lines define a generally circular shape, and the at least one of the series of scanning lines that is between two previously acquired scanning positions comprises at least one radial scanning line having a beginning location that is between a beginning location of two previously acquired scanning lines along the generally circular shape of beginning locations of the series of radial scanning lines.

15. The system of claim 11, wherein the profile estimation module estimates the profile by estimating a location of a peak of a normalized cross-correlation between spatially adjacent scans.

16. The system of claim 11, wherein the profile estimation module estimates the profile by ordering the OCT data in a spatial order.

17. The system of claim 11, wherein the OCT scanner is configured to acquire the OCT data in an ocular region having an diameter of about 6 mm during an acquisition time, and the data locations are temporally distributed so that a selected region having an area of about 0.2 mm$^2$ includes a subset of the plurality of data locations that is generally evenly distributed over the acquisition time.

18. The system of claim 11, herein the OCT scanner is configured to acquire the OCT data in an area of the sample during an acquisition time, and the data locations are temporally distributed so that a selected region of the sample having an area of about one-tenth the area of sample includes a subset of the plurality of data locations that is generally evenly distributed over the acquisition time.

19. The system of claim 11, wherein the OCT scanner is configured to acquire the OCT data in an ocular region having a diameter of about 6 mm during an acquisition time, and the data locations are temporally distributed so that a selected region having an area of about 0.2 mm$^2$ includes a subset of the plurality of data locations that includes a number of data locations acquired during a first quarter of the acquisition time that is generally equal to a number of data locations acquired during a last quarter of the acquisition time.

20. The system of claim 11, wherein herein the OCT scanner is configured to acquire the OCT data in an area of the sample during an acquisition time, and the data locations are temporally distributed so that a selected region of the sample having an area of about one-tenth the area of sample includes a subset of the plurality of data locations that includes a number of data locations acquired during a first quarter of the acquisition time that is generally equal to a number of data locations acquired during a last quarter of the acquisition time.

21. A computer program product for reducing motion artifacts in an Optical Coherence Tomography (OCT) system, the computer program product comprising a non-transient computer readable medium having computer readable program code embodied therein, the computer readable program code comprising:

computer readable program code that is configured to scan a sample with an OCT scanner using a scan pattern to acquire OCT data at a plurality of data locations, the data locations being distributed in the scan pattern across the sample such that at least some spatially adjacent data locations are acquired non-sequentially in time; and computer readable program code that is configured to estimate a profile of the sample corresponding to a sample surface or an aspect of an internal structure of the sample responsive the OCT data.

22. The computer program product of claim 21, wherein the computer readable program code configured to scan the sample by controlling an OCT scanner comprises:

computer readable program code that is configured to scan the sample with a series of scanning lines such that at least one of the series of scanning lines is between two previously acquired scanning lines.

23. The computer program product of claim 22, wherein the series of scanning lines comprises a raster scan such that each of the series of scanning lines comprises a series of generally parallel scan lines, and at least one of the series of generally parallel scanning lines is between two previously acquired scanning lines.

24. The computer program product of claim 22, wherein the series of scanning lines comprises a series of radial scanning lines, beginning locations of the series of radial scanning lines define a generally circular shape, and the at least one of the series of scanning lines that is between two previously acquired scanning positions comprises at least one radial scanning line having a beginning location that is between a beginning location of two previously acquired scanning lines along the generally circular shape of beginning locations of the series of radial scanning lines.

25. The computer program product of claim 21, wherein the computer readable program code configured to estimate a profile comprises computer readable program code configured to estimate a location of a peak of a normalized cross-correlation between spatially adjacent scans.

26. The computer program product of claim 21, wherein the computer readable program code configured to estimate a profile comprises computer readable program code configured to order the OCT data in a spatial order.

27. The computer program product of claim 21, wherein the computer readable program code configured to scan the sample by controlling an OCT scanner comprises:

computer readable program code that is configured to acquire the OCT data in an ocular region having an diameter of about 6 mm during an acquisition time, and the data locations are temporally distributed so that a selected region having an area of about 0.2 $mm^2$ includes a subset of the plurality of data locations that is generally evenly distributed over the acquisition time.

28. The computer program product of claim 21, wherein the computer readable program code configured to scan the sample by controlling an OCT scanner comprises:

computer readable program code that is configured to acquire the OCT data in an area of the sample during an acquisition time, and the data locations are temporally distributed so that a selected region of the sample having an area of about one-tenth the area of sample includes a subset of the plurality of data locations that is generally evenly distributed over the acquisition time.

29. The computer program product of claim 21, wherein the computer readable program code configured to scan the sample by controlling an OCT scanner comprises:

computer readable program code that is configured to acquire the OCT data in an ocular region having a diameter of about 6 mm during an acquisition time, and the data locations are temporally distributed so that a selected region having an area of about 0.2 $mm^2$ includes a subset of the plurality of data locations that includes a number of data locations acquired during a first quarter of the acquisition time that is generally equal to a number of data locations acquired during a last quarter of the acquisition time.

30. The computer program product of claim 21, wherein the computer readable program code configured to scan the sample by controlling an OCT scanner comprises:

computer readable program code that is configured to acquire the OCT data in an area of the sample during an acquisition time, and the data locations are temporally distributed so that a selected region of the sample having an area of about one-tenth the area of sample includes a subset of the plurality of data locations that includes a number of data locations acquired during a first quarter of the acquisition time that is generally equal to a number of data locations acquired during a last quarter of the acquisition time.

\* \* \* \* \*

UNITED STATES PATENT AND TRADEMARK OFFICE
CERTIFICATE OF CORRECTION

PATENT NO. : 8,403,481 B2  
APPLICATION NO. : 13/010517  
DATED : March 26, 2013  
INVENTOR(S) : Izatt et al.

Page 1 of 1

It is certified that error appears in the above-identified patent and that said Letters Patent is hereby corrected as shown below:

On Title Page:
Item 75, Inventors: correct "Ryan P. McNabb, Durhham, NC (US);"
to read -- Ryan P. McNabb, Durham, NC (US); --

In the Claims:
Column 20, Claim 18, Line 39: correct "claim 11, herein the OCT"
to read -- claim 11, wherein the OCT --

Column 20, Claim 20, Line 55: correct "claim 11, wherein herein the OCT"
to read -- claim 11, wherein the OCT --

Signed and Sealed this
Third Day of February, 2015

Michelle K. Lee
*Deputy Director of the United States Patent and Trademark Office*